US006548085B1

(12) United States Patent
Zobitne et al.

(10) Patent No.: US 6,548,085 B1
(45) Date of Patent: Apr. 15, 2003

(54) INSECTICIDAL COMPOSITIONS AND METHOD OF CONTROLLING INSECT PESTS USING SAME

(75) Inventors: Karen A. Zobitne, Middleton, PA (US); Michael J. Gehret, Lititz, PA (US)

(73) Assignee: Woodstream Corporation, Lititz, PA (US)

( * ) Notice: Subject to any disclaimer, the term of this patent is extended or adjusted under 35 U.S.C. 154(b) by 0 days.

(21) Appl. No.: 09/281,268

(22) Filed: Mar. 30, 1999

Related U.S. Application Data

(63) Continuation-in-part of application No. 09/060,141, filed on Apr. 15, 1998, now Pat. No. 5,998,484.

(51) Int. Cl.[7] .................. A01N 65/00; A01N 61/00; A01N 41/02; A01N 57/02; A01N 25/30

(52) U.S. Cl. .................. 424/725; 424/736; 424/739; 424/742; 424/745; 424/746; 424/747; 424/750; 424/754; 424/757; 424/766; 424/768; 424/769; 424/770; 424/773; 424/774; 424/778; 424/779; 514/78; 514/578; 514/709; 514/711; 514/729; 514/762; 514/763; 514/768; 514/772; 514/975

(58) Field of Search .................. 424/195.1, 196.1, 424/43, 45, 725, 736, 739, 742, 745, 746, 747, 750, 754, 757, 768, 769, 770, 773, 774, 778, 766, 779; 514/78, 711, 729, 762, 763, 768, 772, 975, 709

(56) References Cited

U.S. PATENT DOCUMENTS

| | | | |
|---|---|---|---|
| 351,897 A | 11/1886 | Boyer .................. 424/416 |
| 1,630,836 A | 5/1927 | Drushel .................. 424/701 |
| 2,898,267 A | 8/1959 | Lindner .................. 514/568 |
| 3,321,364 A | 5/1967 | Kessler .................. 424/195.1 |
| 3,887,710 A | 6/1975 | Shaver et al. .................. 514/479 |
| 4,000,266 A | 12/1976 | Incho .................. 514/461 |
| 4,164,561 A | 8/1979 | Hautmann .................. 424/416 |
| 4,193,986 A | 3/1980 | Cox .................. 424/411 |
| 4,195,080 A | 3/1980 | Herrera et al. .................. 424/195.1 |
| 4,368,207 A | 1/1983 | Lover et al. |
| 4,518,593 A | * 5/1985 | Juvin et al. .................. 424/195 |
| 4,587,123 A | 5/1986 | Price .................. 424/195.1 |
| 4,627,850 A | 12/1986 | Deters et al. .................. 604/892.1 |
| 4,637,830 A | 1/1987 | Dyer et al. .................. 504/141 |
| 4,671,960 A | 6/1987 | Thielen et al. .................. 424/195.1 |
| 4,678,775 A | 7/1987 | Nathanson .................. 514/47 |
| 4,721,706 A | 1/1988 | Bessler et al. .................. 514/78 |
| 4,721,727 A | 1/1988 | Mikolajczak et al. ....... 514/473 |
| 4,735,358 A | 4/1988 | Morita et al. .................. 239/1 |
| 4,767,882 A | 8/1988 | Suzukamo et al. .......... 560/100 |
| 4,874,610 A | 10/1989 | Cousin .................. 424/196.1 |
| 4,891,222 A | 1/1990 | Eichhoefer .................. 424/196.1 |
| 4,933,181 A | 6/1990 | Brown et al. .................. 424/405 |
| 4,933,371 A | 6/1990 | Hink et al. .................. 514/739 |
| 4,968,666 A | 11/1990 | Sugi .................. 424/405 |
| 5,079,000 A | 1/1992 | Takahashi et al. ........ 424/195.1 |
| 5,104,658 A | 4/1992 | Hagarty .................. 424/405 |
| 5,106,622 A | 4/1992 | Sherwood et al. ........ 424/195.1 |
| 5,110,594 A | 5/1992 | Morita .................. 424/405 |
| 5,118,506 A | 6/1992 | Eichhoefer .................. 424/196.1 |
| 5,192,545 A | 3/1993 | Nakashima .................. 424/405 |
| 5,196,200 A | 3/1993 | Wilson .................. 424/405 |
| 5,208,029 A | 5/1993 | Plummer et al. .......... 424/405 |
| 5,216,009 A | 6/1993 | Fujimoto et al. .......... 514/406 |
| 5,240,708 A | 8/1993 | Plummer et al. .......... 424/405 |
| 5,242,907 A | 9/1993 | Dawson .................. 514/65 |
| 5,273,953 A | 12/1993 | Szekely et al. ............. 504/116 |
| 5,277,836 A | 1/1994 | Peters .................. 252/143 |
| 5,288,632 A | 2/1994 | Pannell .................. 435/243 |
| 5,346,704 A | 9/1994 | Lajoie .................. 424/717 |
| 5,372,817 A | 12/1994 | Locke et al. .................. 424/405 |

(List continued on next page.)

FOREIGN PATENT DOCUMENTS

| | | |
|---|---|---|
| DE | 3901341 | 7/1990 |
| DE | 4231045 | 3/1994 |
| DE | 198 25 605 | 12/1999 |
| EP | 512328 | * 11/1992 |
| EP | 0 629 345 | 12/1994 |
| FR | 2 634 103 | 1/1990 |
| JP | 53-47532 | * 4/1978 |
| WO | 85/05038 | 11/1985 |
| WO | 93/00811 | 1/1993 |
| WO | 94/27434 | 12/1994 |
| WO | 94/27566 | * 12/1994 |
| WO | 99/63818 | 12/1999 |

OTHER PUBLICATIONS

Chemical Abstracts 89: 175028, abstracting JP 53–47532, 1978.*

Chemical Abstracts 131:307910, 1999.

Patent Abstracts of Japan, JP 52 110 823 A, *Repellent*, Sep. 17, 1977.

Patent Abstracts of Japan, JP 59 222 402, *Insecticide Composition*, Dec. 14, 1984.

Patent Abstracts of Japan, JP 01 016 706 A, *Insecticidal Composition*, Jan. 20, 1989.

Patent Abstracts of Japan, JP 02 049 703 A, *Composition for Controlling Minamikiroazamiuma (Insect Pest of Thrips Having Invaded from Southeastern Asia) and Control*, Feb. 20, 1990.

Patent Abstracts of Japan, JP 04 059 703, *Miticide*, Feb. 26, 1992.

(List continued on next page.)

Primary Examiner—John Pak
(74) Attorney, Agent, or Firm—Jacobson Holman PLLC

(57) ABSTRACT

A synergistic insecticide is provided by the addition of sodium lauryl sulfate or lecithin to an essential oil, preferably an essential oil which has been deregulated by the Environmental Protection Agency, to enable independently inactive or relatively inactive materials to provide commercially acceptable insecticidal properties without the need for undesirable poisons that may be toxic to humans and pets.

62 Claims, 15 Drawing Sheets

U.S. PATENT DOCUMENTS

| | | | |
|---|---|---|---|
| 5,403,587 A | 4/1995 | McCue et al. | 424/195.1 |
| 5,439,690 A | 8/1995 | Knight | 424/687 |
| 5,449,517 A | 9/1995 | Fitzjarrell | 424/195.1 |
| 5,474,898 A | 12/1995 | Venter et al. | 435/6 |
| 5,489,433 A | 2/1996 | Aboud | 424/405 |
| 5,518,736 A | 5/1996 | Magdassi et al. | 424/451 |
| 5,547,918 A | 8/1996 | Newton et al. | 504/116 |
| 5,556,881 A | 9/1996 | Gran Marisi | 514/557 |
| 5,569,411 A | 10/1996 | Steltenkamp et al. | 510/383 |
| 5,573,700 A | 11/1996 | Steltenkamp et al. | 252/173 |
| 5,653,991 A | 8/1997 | Rod | 424/406 |
| 5,658,954 A | 8/1997 | Targosz | 514/617 |
| 5,676,958 A | 10/1997 | Emerson | 424/405 |
| 5,681,859 A | 10/1997 | James et al. | 514/625 |
| 5,683,971 A | 11/1997 | Rose et al. | 510/130 |
| 5,693,344 A | 12/1997 | Knight et al. | 424/687 |
| 5,990,157 A | 11/1999 | Zocchi et al. | 514/464 |
| 6,001,874 A | 12/1999 | Veierov | 514/533 |
| 6,004,569 A | 12/1999 | Bessette et al. | 424/406 |
| 6,114,384 A | 9/2000 | Bessett et al. | 514/546 |
| 6,231,865 B1 * | 5/2001 | Hsu et al. | 424/195.1 |
| 6,277,389 B1 * | 8/2001 | Pullen | 424/405 |

OTHER PUBLICATIONS

Patent Abstracts of Japan, JP 04 091 003 A, *Mite Controlling Agent*, Mar. 24, 1992.

Patent Abstracts of Japan, JP 04 149 103 A, *Controlling Agent of Indoor Dust–Type Mite*, May 22, 1992.

Patent Abstracts of Japan, JP 05 039 203 A, *Composition for Mite Control*, Feb. 19, 1993.

Merck Index, 11$^{th}$ Edition, pp. 176, 612–613 and 1146–1147 (1989).

Deshpande, et al., *Stored Grain Pest Control Agents from Nigella Sativa and Pogostemon Heyneanus*, Bull. Grain Technol., vol. 12(3), 1974, pp. 232–234.

Hollingworth, R.M., *The Biochemical and Physiological Basis of Selective Toxicity*, Insecticide Biochemistry and Physiology, C.F. Wilkinson (ed.), Plenum Press, New York, 1976, pp. 431–447.

Metcalf, et al. (ed.), *The Future for Insecticides, Needs and Prospects*, Wiley–Interscience, New York, 1976, pp. 97–113.

Fields, et al., *Phototoxins as Insecticides and Natural Plant Defences*, Mem. Entomol. Soc. Canada, 159:29–38, 1991.

Mitsui, et al., *Search for Insect Growth Regulators*, Rev. Pestic. Toxicol., 1:239–247, 1991.

Rice, et al., *Structural Requirements for Monoterpenoid Activity against Insects*, Bioregulators for Crop Protection and Pest Control, ACS Symposium Series 557, Chapter 8, pp. 92–108 (1994).

Escoubas, et al., *Insecticidal and Antifeedant Activities of Plant Compounds, Potential Leads for Novel Pesticides*, Natural and Engineered Pest Management Agents, American Chemical Society Symposium Series 551:162–171, 1994.

Lowery, et al., *Insect growth regulating effects of neem extract and azadirachtin on aphids*, Entomol. Exp. Appln. 72–77–84, 1994.

Tsao, et al., *Monoterpenoids and Their Synthetic Derivatives as Leads for New Insect–Control Agents*, ACS Symposium Series, 584, Chapter 28, pp. 312–324 (1995).

Dev, et al., *Insecticides of Natural Origin*, Harwood Academic Publishers, Amsterdam 1997, pp. vii, viii, 5 and 47–58.

K. Gunathilagaraj, et al., Laboratory Evaluation of Toxicity of Clvoe Oil to *Callosobruchus chinensis* (L.) on Greengram Seeds, Madras agric. J. 65(7): 487–488, Jul. 1978.

C. Marcus, et al., Biologically Active Components of Anise: Toxicity and Interactions with Insecticides in Insects, J. Agric. Food Chem., vol. 27, No. 6, 1979.

M.T. Stephen Hsia, et al., Microbial Mutagenicity Studies of Insect Growth Regulators and Other Potential Insecticidal Compounds in *Salmonella Typhimurium*, Chemosphere, No. 8, pp. 521–529, 1979.

N.K. Gulati, et al., Biological Application of Essential Oils, Indian Perfumer, vol. 26, Nos. 2–4, pp. 241–248, 1982.

D. Singh, et al., Cedarwood Oil as a Potential Insecticidal Agent against Mosquitos, Naturwissenschaften 71, pp. 265–266, 1984.

M. Saleh, A Desert Plant from Egypt, *Anabasis setifera*: An Efficient Natural Factory of Carvacrol and Thymol, J. Agric. Food Chem, 34, pp. 192–194, 1986.

B.P. Saxena, et al., Essential Oils and Insect Control, Cultivation and Utilization of Aromatic Plants, pp. 766–776, 1989.

B.A. Ansari, et al., Toxicity of Some Essential Oils Against the Pulse Beetle, *Callosobruchus maculatus* (F.) (Coleoptera: Bruchidae), J. Inst. Agric. Anim. Sci., vol. 11:95–98, pp. 95–98, 1990.

J. Coats, et al., Toxicity and Neurotoxic Effects of Monoterpenoids in Insects and Earthworms, Naturally Occurring Pest Bioregulators, pp. 305–316, 1991.

N.E.S. Lale, The biological effects of three essential oils on *Callosobruchus maculatus* (F.) (Coleoptera: Bruchidae), Journal of African Zoology, pp. 357–362, Feb. 15, 1991.

I. Konstantopoulou, et al., Insecticidal effects of essential oils. A study of the effects of essential oils extracted from eleven Greek aromatic plants on *Drosophila auraria*, Experientia, 1992.

J. Grossman, Botanical Pesticides in Africa, The IPM Practictioner, 1992 Index Issue.

M. Bhatnagar, et al., Laboratory evaluation of insecticidal properties of *Ocimum basilicum* Linnaeus and *O. sanctum* Linneaus plant's essential oils and their major constituents against vector mosquito species, J. ent. Res., 17(1): 21–26, 1993.

R.S. Farag, et al., Insecticidal Activity of Thyme and Clove Essential Oils and Their Basic Compounds on Cotton Leaf Worm (*Spodoptera Littoralis*), Bull Fac. Agric. Univ. Cairo, 45, pp. 207–230, 1994.

P. Rice, et al., Insecticidal Properties of Several Monoterpenoids to the House Fly (Diptera: Muscidae), Red Flour Beetle (Coleoptera: Tenebrionidae), and Southern Corn Rootworm (Coleoptera: Chrysomelidae), Journal of Economic Entomology, pp. 1172–1179, 1994.

G. Singh, Essential Oils: A potent source of natural pesticides, J. Scientific & Industrial Research, vol. 52(10), 1993, pp. 676–678.

King, "Chemicals Evaluated as Insecticides and Repellents at Orlando, Fla.", Agriculture Handbook No. 69, pp. 1–17, tables 244–249 (1954).

Abstract—Indian Journal of Agronomy 38(3):443–448 (Date Unavailable).

Abstract—Journal of the Indian Society of Soil Science 41(1): 176–177 (Date Unavailable).

Abstract—Int'l. Journal of Food Sciences and Nutrition, 46(3):225–228 (Date Unavailable).

Abstract—Plant Foods for Human Nutrition (Dordrect), 47(2)109–114 (Date Unavailable).

Abstract—Journal of Advanced Zoology 16(2): 85–87 (Date Unavailable).

Abstract—Fertilizer Research 44(1):17–21 (Date Unavailable).

* cited by examiner

Black Ant Kill Time Study

Black Ant Kill Time Study

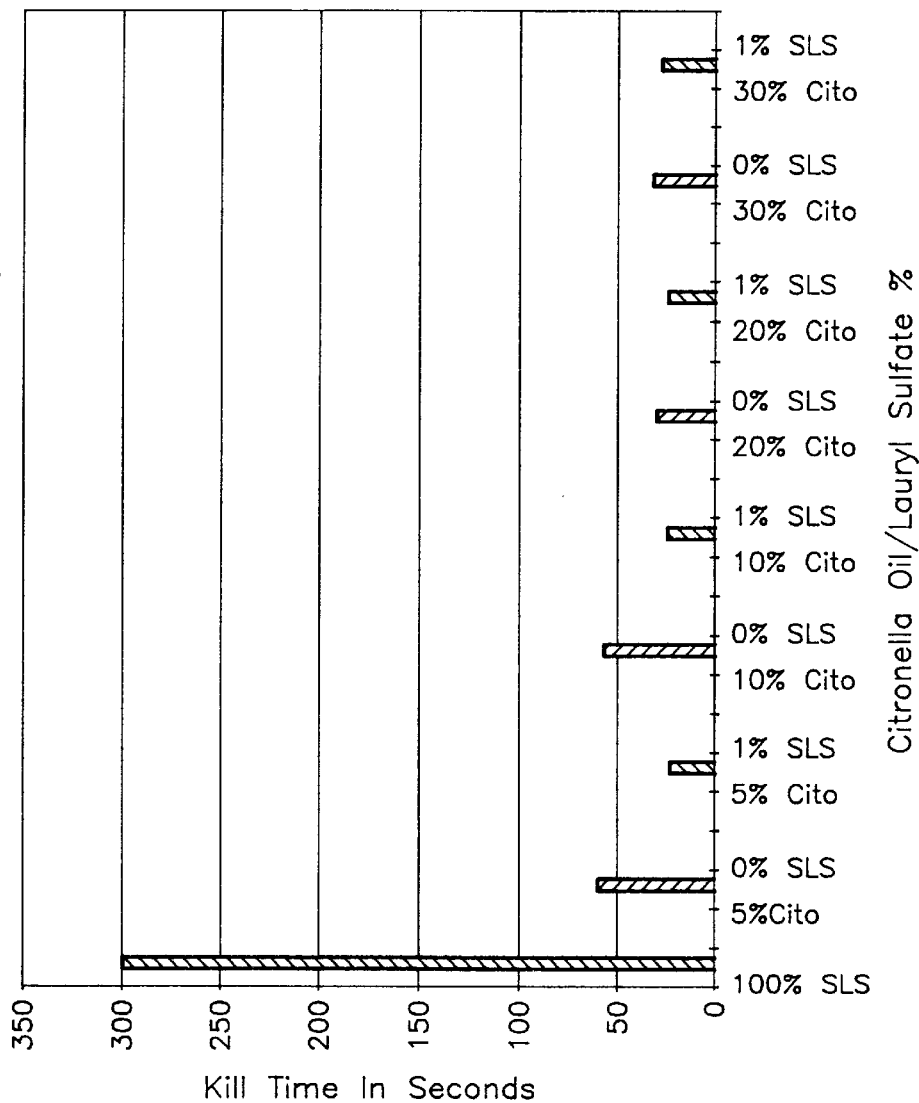

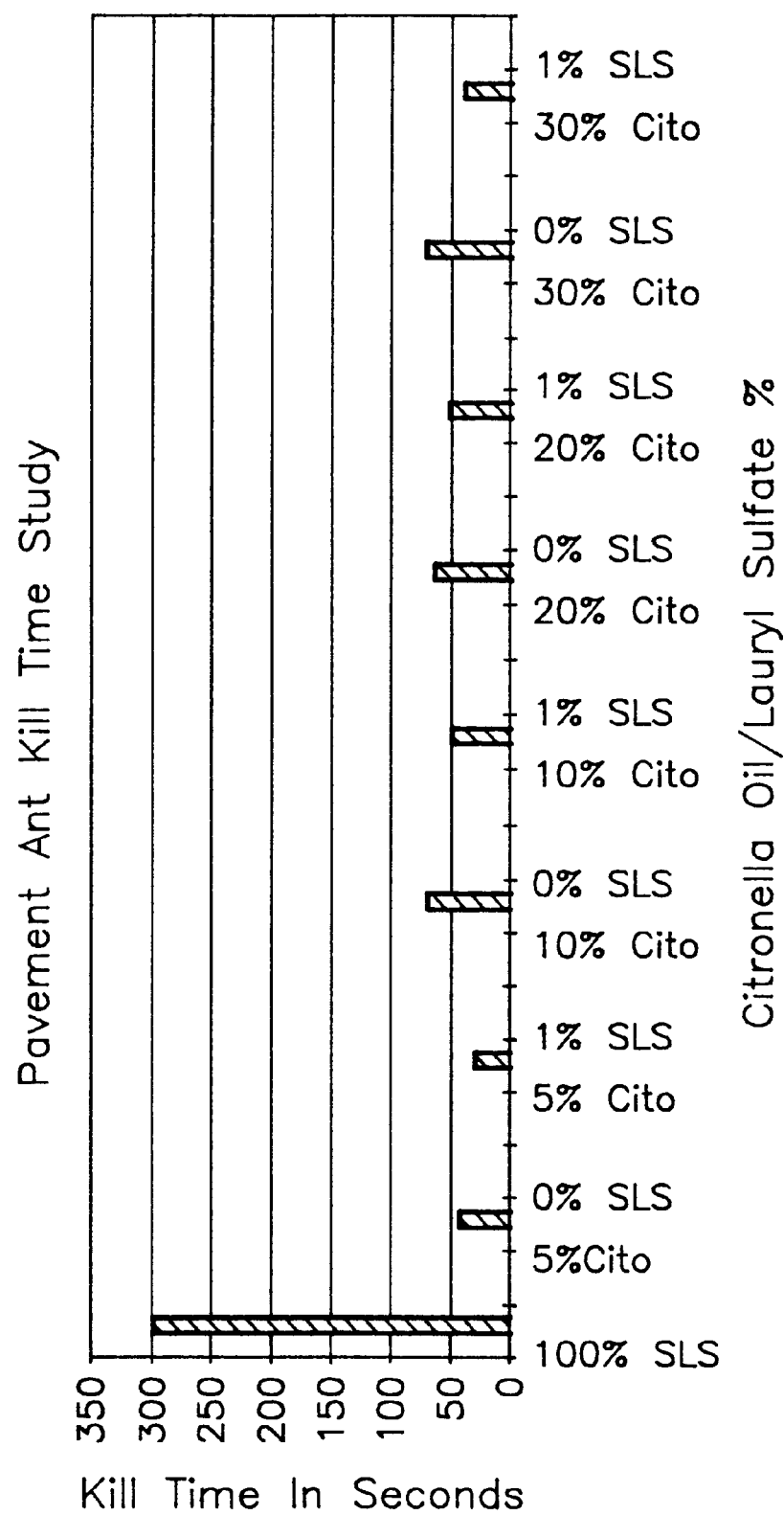

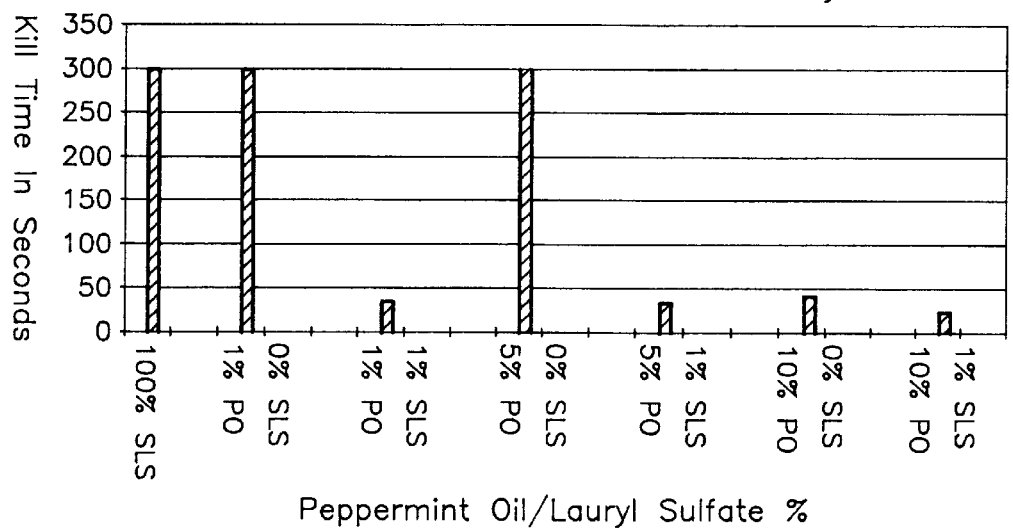
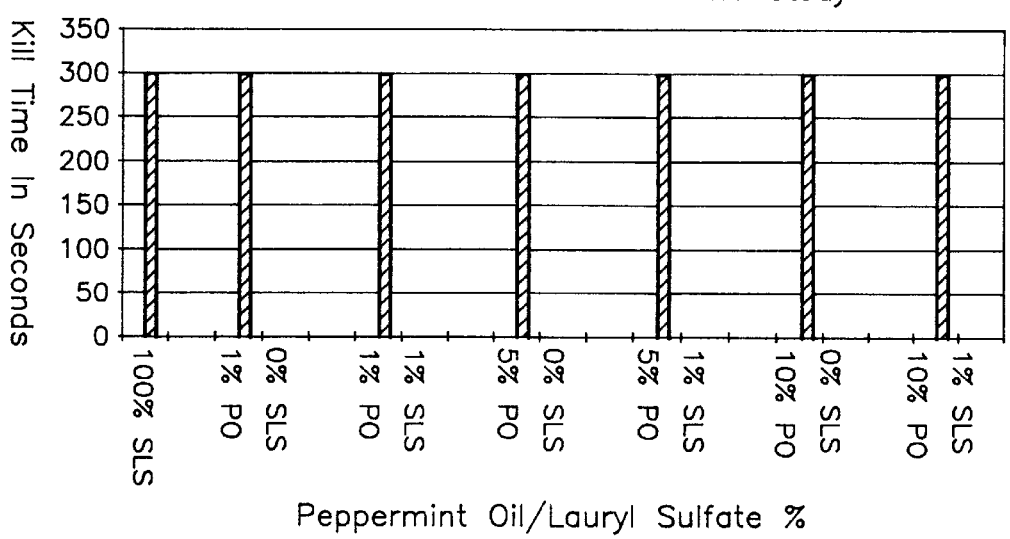

Pavement Ant Kill Time Study

German Cockroach Kill Time Study

German Cockroach Kill Time Study

American Cockroach Kill Time Study

Pavement Ant Kill Time Study

German Cockroach Kill Time Study

German Cockroach Kill Time Study

American Cockroach Kill Time Study

American Cockroach Kill Time Study

Pavement Ant Kill Time Study

INSECTICIDAL COMPOSITIONS AND METHOD OF CONTROLLING INSECT PESTS USING SAME

RELATED APPLICATION

This application is a continuation-in-part of application Ser. No. 09/060,141 filed Apr. 15, 1998 which is now U.S. Pat. No. 5,998,484, the subject matter of which is incorporated herein in its entirety.

BACKGROUND OF THE INVENTION

This invention relates to insecticidal compositions and methods of using same to control various crawling and flying insect pests, and, in its preferred embodiments, relates more particularly to synergistic "non-poison" insecticides adapted to unexpectedly increase insect mortality and reduce kill time.

Commercially available insecticides, including those available for home use, commonly comprise active ingredients or "poisons" which are not only toxic to the target insect pests, but, if used in relatively confined environments and delivered as aerosol sprays, can be present in sufficient concentration to also be toxic to humans and household pets. Various undesirable side effects may include immediate or delayed neurotoxic reactions, and/or suffocation. Even the noxious odor of such materials can cause headaches or upset stomachs in some individuals. These adverse side effects are exacerbated when such compositions come in contact with persons of increased sensitivity, or persons of small body mass such as children or babies.

For some time, efforts have been made to develop insecticidal compositions, particularly those intended for residential use in aerosol form, which are effective in killing the targeted insect pests completely and quickly, but non-toxic to humans and pets. The Environmental Protection Agency (EPA) regulates the use of potentially toxic ingredients in pesticidal compositions under the Federal Insecticide, Fungicide and Rodenticide Act. Certain materials considered to be either active or inert materials by the EPA have been deregulated or otherwise identified as acceptable "safe" substances offering minimum risk in normal use. Other materials are currently undergoing investigation and may be deregulated in due course. Deregulated substances are generally considered non-poisonous by the consumer. Thus, the term "non-poisonous" as used herein is intended to convey a composition that, while highly effective in killing targeted insect pests, is safe to use around humans, particularly small children, and pets.

Unfortunately, non-poisonous insecticidal compositions available heretofore incorporating deregulated materials as the active ingredient have had limited efficacy. Attempts to use deregulated essential oils as the active ingredient in such insecticides, while having limited success, have generally been found to be either cost prohibitive, inadequately lethal to control a range of targeted insect pest species, or too slow-acting to enable the user to confirm that the insect has been killed and to dispose of the dead insect so as to avoid polluting the environment.

Among the insects which are found to be particularly undesirable are cockroaches, both the American and German species. These pests shed their "skin" which, over time, disintegrates forming what is known as "cuticle" in the air, a particular problem for people suffering from asthma. Thus, not only is it important to kill cockroaches with an effective insecticide, the kill time must be sufficiently short for the carcass to be properly disposed of before the insect can crawl into a remote area to die.

While cockroaches are a prime target for a household spray, for general application such materials must also be effective against other crawling insects, such as ants, water bugs, silverfish, crickets, spiders and centipedes. Additionally, aerosol compositions of such insecticides of proper concentration must also be effective against various flying insects, including flies, mosquitoes, gnats, moths, wasps, hornets, yellow jackets and other bees, both inside and outside of the house.

Among the materials exempted by the EPA is cornmint oil (also known as Japanese mint or *Mentha arvensis*). Cornmint oil includes a high concentration of menthol and is known to contain alpha-pinene, myrcene, limonene, gamma-terpenine, 3-octanol, menthofuran, beta-caroyophyllene, germa-crene D and beta-pinene, along with other components. As with other mint oils, cornmint oil has been used as a flavorant in mouthwashes, cough syrups, throat lozenges, chewing gum, and the like.

While cornmint oil has been considered for its insecticidal or insect repellent properties, it has not been shown to be particularly effective, and certainly has not been distinguished from other materials of this kind as a candidate for special attention.

Other essential oils currently deregulated by the EPA include cedar oil, cinnamon oil, citronella oil, clove oil, corn oil, garlic oil, lemongrass oil, linseed oil, peppermint oil, rosemary oil, soybean oil and thyme oil. Among the essential oils proposed for exemption from registration are a number of the citrus oils. Citrus oils would include orange oil, lemon oil, lime oil, grapefruit oil and tangerine oil.

As with the cornmint oil, some of these other essential oils have been considered for their insecticidal or insect repellent properties, but they have not been shown to be particularly effective as active ingredients. It would, therefore, be both environmentally and commercially important to be able to enhance the insecticidal properties of these relatively safe essential oils by incorporating an otherwise ineffective, but environmentally friendly, synergist to increase the activity of the resultant composition to a level sufficient to quickly produce significant mortality in at least certain insect populations.

SUMMARY OF THE INVENTION

It is a primary object of the instant invention to provide a non-poisonous broad-spectrum insecticide containing, as an essential active ingredient, materials that have been approved by the EPA as safe or as offering minimum risk in products of this nature. Consistent with this objective, this invention provides an aerosol insecticide which is not detrimental to the health of humans or pets and which is environmentally safe, yet effective in killing targeted insect pests with which it comes in contact.

Another object of the instant invention is the provision of an insecticidal composition that not only effectively kills 100% of the targeted insects with which it comes in contact, but kills such insects within seconds of contact so that the user can be certain of the effectiveness of the insecticide, and the insect carcass can be safely and easily disposed of without contaminating the environment.

Yet a further object of this invention is the provision of an insecticidal composition comprising a combination of ingredients which individually are relatively ineffective, but act in concert to provide high total killing power with a substantially decreased kill time.

A still further object of this invention is the provision of a pesticide, comprising an essential oil, the activity of which has been unexpectedly enhanced by the incorporation of insecticidally effective quantities of sodium lauryl sulfate or lecithin, so as to surprisingly improve both the kill ratio and kill time, providing greater insecticidal activity than either of the ingredients and more effective and faster-acting killing power than would be expected by combining these components.

Yet another object of this invention is the provision of an insecticidal composition comprising an essential oil, preferably one selected from the group consisting of cedar oil, cornmint oil, cinnamon oil, citronella oil, lemongrass oil, peppermint oil, orange oil, lemon oil, lime oil, grapefruit oil and tangerine oil, in synergistic combination with sodium lauryl sulfate or lecithin to enhance the effectiveness of the composition sufficiently to render the otherwise relatively ineffective individual components functionally enhanced and quicker-acting, thereby improving both the mortality and the kill time. Among the deregulated essential oils, cedar oil and cornmint oil are particularly attractive because of their pleasant odors.

Another object of this invention is the provision of an insecticidal composition comprising an essential oil and a synergist which minimizes the quantity of the active ingredient necessary to effect acceptable mortality rates in at least some insect populations, even further reducing the cost and dangers of using such materials by the general public.

Yet another object of the invention is the provision of a non-poisonous, highly effective insecticidal composition, which may be sprayed in aerosol form from a standard pump dispenser or, which may incorporate a propellant such as carbon dioxide ($CO_2$) or the like in a pressurized container of conventional design, so that the composition may be sprayed directly onto a crawling or flying insect pest.

Another object of this invention is the provision of an insecticidal composition of the type described incorporating mineral oil or other such material to retain the essential active ingredients on a contacted surface for residual killing power over an extended period of time.

Consistent with the foregoing objectives, all of the essential oils tested herein show synergistic insecticidal improvement in combination with sodium lauryl sulfate at some level of concentration against at least some of the targeted insects tested and, therefore, may have particular utility as a pesticide intended for one or more specific insect populations. Moreover, other essential oils that have been deregulated by the EPA are expected to provide similar results and lecithin, considered a deregulated inert material by the EPA, is expected to function as a synergist with the essential oils much like sodium lauryl sulfate.

These and other objects of the invention, as well as many of the attendant advantages thereof, will become more readily apparent when reference is made to the following detailed description of the preferred embodiments which refers to the accompanying drawings.

BRIEF DESCRIPTION OF THE INVENTION

FIG. 7 is a bar graph illustrating the insecticidal effects of combining citronella oil with sodium lauryl sulfate in killing German cockroaches.

FIG. 9 is a bar graph illustrating the insecticidal effects of combining citronella oil with sodium lauryl sulfate in killing pavement ants.

FIG. 10 is a bar graph illustrating the insecticidal effects of combining peppermint oil with sodium lauryl sulfate in killing German cockroaches.

FIG. 11 is a bar graph illustrating the insecticidal effects of combining peppermint oil with sodium lauryl sulfate in killing American cockroaches.

DETAILED DESCRIPTION OF THE PREFERRED EMBODIMENTS

Figure 1:
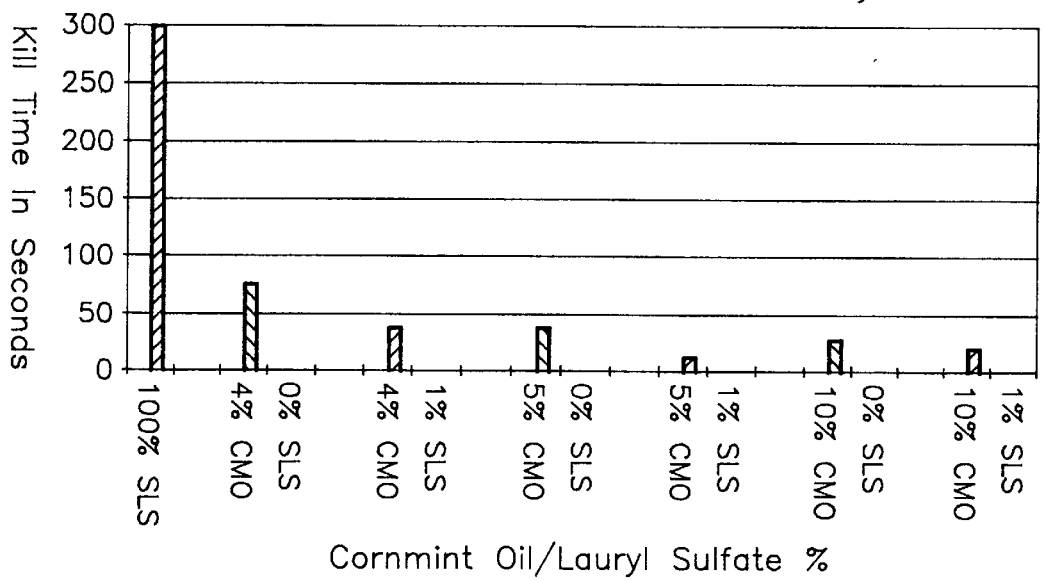
FIG. 1 is a bar graph illustrating the insecticidal effects of combining cornmint oil with sodium lauryl sulfate in killing German cockroaches.

In describing a preferred embodiment of the invention specific terminology will be resorted to for the sake of clarity. However, the invention is not intended to be limited to the specific terms so selected, and it is to be understood that each specific term includes all technical equivalents which operate in a similar manner to accomplish a similar purpose.

In its broadest aspects, the essential active ingredients in the composition of the instant invention comprise a combination, in insecticidally effective proportions, of an essential oil, preferably a deregulated essential oil, and a deregulated synergist selected from the group consisting of sodium lauryl sulfate and lecithin. The active ingredients may be dissolved in an inert carrier such as water and dispensed in a conventional manner, e.g., from a standard pump-spray container. Alternatively, and preferably, the aqueous insecticidal composition may be packaged in a pressurized container such as a conventional aerosol can or the like, utilizing an expandable gas, such as carbon dioxide ($CO_2$) as a propellant in a well known manner.

For optimum effectiveness, the insecticidal composition of this invention is sprayed directly on targeted crawling or flying insect pests in sufficient concentrations to cause death within seconds. A material such as mineral oil may be incorporated into the composition to provide residual killing power on surfaces for up to, as much as, four weeks or more. When the insect pests track through, and come in contact with, previously sprayed product, the active ingredients remain on their bodies and they eventually die. Without the mineral oil, the composition dries, leaving no residue.

The testing described below establishes that sodium lauryl sulfate alone does not kill the targeted insects. Further, in most instances, the tested essential oils alone either do not kill the targeted insects, or if they eventually kill some of the targeted insects, they generally require relatively high concentrations of the essential oil, and/or they are relatively slow-acting. Surprisingly, the test data shows that the addition of sodium lauryl sulfate to the tested essential oils produces a high mortality rate in a relatively short time with reduced concentrations of the active ingredients against at least some of the targeted insects.

As will be seen from the following data, not all of the essential oils tested are effective, even with the addition of sodium lauryl sulfate, to function commercially as an insecticide against all of the targeted insects. In some instances, an essential oil/sodium lauryl composition is highly effective against a particular insect population, but not others. In other instances, synergism is seen against certain targeted insects only at particular concentrations of the active ingredients. Some of these anomalies are technically understood. For example, a counterintuitive decrease in kill time of ants with an increase in concentration of certain essential oils may result from the increased density of the composition and the small body mass of the ants. Other results are unexpected and inexplicable at this time.

As noted, all of these tested essential oils shows synergistic insecticidal activity in combination with sodium lauryl sulfate at least at some concentrations against some of the insects with which they came in contact. Moreover, the use of the synergistic combination of environmentally safe or non-poisonous active ingredients of this invention, or those that are expected to be deregulated by the EPA in due course, has been found to kill at least certain insect populations in a time generally equal to, or shorter than, commercially available insecticides which incorporate well known poisons that, under certain conditions, can be toxic to humans and pets.

To evidence the unexpectedly improved nature of the results obtained using the synergistic insecticidal composition of the instant invention, the following test protocol was established:

Scope

To determine the effectiveness of an essential oil/sodium lauryl sulfate aerosol spray according to this invention as an insecticide when applied directly by a conventional pump spray on German cockroaches, American cockroaches and various ant species.

Materials

Insects shall be healthy and undeformed. Only adult male and female insects shall be used for testing purposes. The insects shall be contained in a 21.5×15.5×5.5 inch testing arena.

Procedure

1. Gather 10 adult insects, 5 males and 5 females.
2. Place 1 insect into the testing arena.
3. Select spray to be tested. Spray cockroaches for 3 seconds, ants for 2 seconds.
4. Record kill time in seconds.
5. Wipe away any spray residue before beginning another test.
6. Repeat steps 2, 3, 4 and 5 until all test insects are used.
7. Record date of testing, type of test material used, type of insect used, kill time in seconds, and whether or not test specimen meets standard.

Following this protocol, aqueous solutions of selected essential oils were prepared at different concentrations, both with and without the addition of sodium lauryl sulfate, and tested for their insecticidal activity (kill time in seconds) against German and American cockroaches and black or pavement ants. The results are tabulated below and illustrated graphically in the accompanying drawings.

Cornmint Oil

TABLE 1

The Effects of Cornmint Oil and Lauryl Sulfate on German Cockroaches

| Test No. | Active Ingredients (Volume %) | Kill Time (Seconds) |
| --- | --- | --- |
| 1. | 100% sodium lauryl sulfate (SLS) | 300[1] |
| 2. | 4% cornmint oil (CMO) 0% SLS | 76.4 |
| 3. | 4% CMO 1% SLS | 38.9 |
| 4. | 5% CMO 0% SLS | 39.8 |
| 5. | 5% CMO 1% SLS | 14.2 |
| 6. | 10% CMO 0% SLS | 30.2 |
| 7. | 10% CMO 1% SLS | 21.2 |

[1]An entry of 300 seconds in these Tables denotes that no deaths occurred during that time frame. For practical purposes, kill times in excess of 300 seconds would be commercially unacceptable. Therefore, for purposes of this protocol, an entry of 300 seconds is considered to be an ineffective insecticide.

Table 1 and FIG. 1 show that sodium lauryl sulfate alone is ineffective as an insecticide against German cockroaches (Test No. 1). Moreover, while cornmint oil alone (Test Nos. 2, 4 and 6) shows some insecticidal activity, the addition of 1% sodium lauryl sulfate dramatically reduces the kill time (compare Test Nos. 2, 4 and 6 with Test Nos. 3, 5 and 7, respectively). An aerosolized benchmark, commercially available insecticide incorporating active ingredients designated by the Environmental Protection Agency as poisons[2] killed German cockroaches in an average of 19.2 seconds. An aerosolized 4% cornmint oil, 1% sodium lauryl sulfate composition according to this invention killed German cockroaches in about 21 seconds, without the need for environmentally undesirable poisons.[3]

[2] RAID® aerosol insecticide manufactured by S.C. Johnson, containing 0.2% pyrethrin, 0.2% permethrin and 0.5% piperonyl butoxide.
[3] The tests shown in the Tables utilized the active ingredients in an aqueous solution dispensed from a standard pump-type sprayer. Shorter kill times result when the insecticide is aerosolized, i.e., dispensed from a pressurized aerosol can using a propellant such as carbon dioxide.

TABLE 2

The Effects of Cornmint Oil and Lauryl Sulfate on American Cockroaches

| Test No. | Active Ingredients (Volume %) | Kill Time (Seconds) |
| --- | --- | --- |
| 8. | 100% SLS | 300 |
| 9. | 4% CMO 0% SLS | 300 |
| 10. | 4% CMO 1% SLS | 45.2 |
| 11. | 5% CMO 0% SLS | 300 |
| 12. | 5% CMO 1% SLS | 42.2 |
| 13. | 10% CMO 0% SLS | 300 |
| 14. | 10% CMO 1% SLS | 37.8 |

Figure 2:
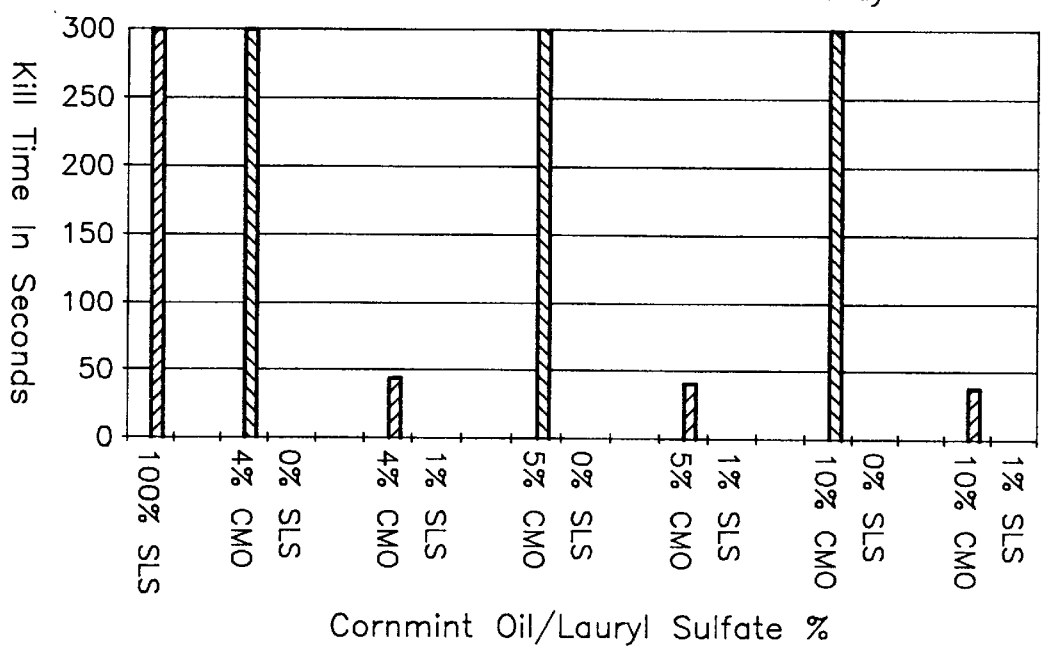
FIG. 2 is a bar graph illustrating the insecticidal effects of combining cornmint oil with sodium lauryl sulfate in killing American cockroaches.

As seen from the above data and as graphically illustrated in FIG. 2, neither sodium lauryl sulfate alone (Test No. 8) nor cornmint oil alone (Test Nos. 9, 11 and 13), kills American cockroaches within the 300 second standard test time allotted. The addition of 1% sodium lauryl sulfate to a 4, 5 or 10% cornmint oil composition (Test Nos. 10, 12 and 14) show 100% effectiveness in killing the targeted insects within the test time.

Had the insecticidal compositions of this invention used in Test Nos. 10, 12 and 14 above been aerosolized, kill times of even less than 45.2 sec., 42.2 sec. and 37.8 sec. would be expected. In contrast, the aerosolized benchmark commercially available insecticide referred to above averaged 197.2 seconds to kill American cockroaches.

Thus, the combination of non-poisonous ingredients in the insecticidal composition of this invention effectively killed American cockroaches when the individual components were "not effective" and, did so in substantially less time than even a poison-containing commercial aerosol.

TABLE 3

The Effects of Cornmint Oil and Lauryl Sulfate on Black Ants

| Test No. | Active Ingredients (Volume %) | Kill Time (Seconds) |
| --- | --- | --- |
| 15. | 100% SLS | 300 |
| 16. | 4% CMO 0% SLS | 87 |
| 17. | 4% CMO 1% SLS | 12.9 |
| 18. | 5% CMO 0% SLS | 72.9 |
| 19. | 5% CMO 1% SLS | 40.7 |
| 20. | 10% CMO 0% SLS | 49.4 |
| 21. | 10% CMO 1% SLS | 27 |

Figure 3:
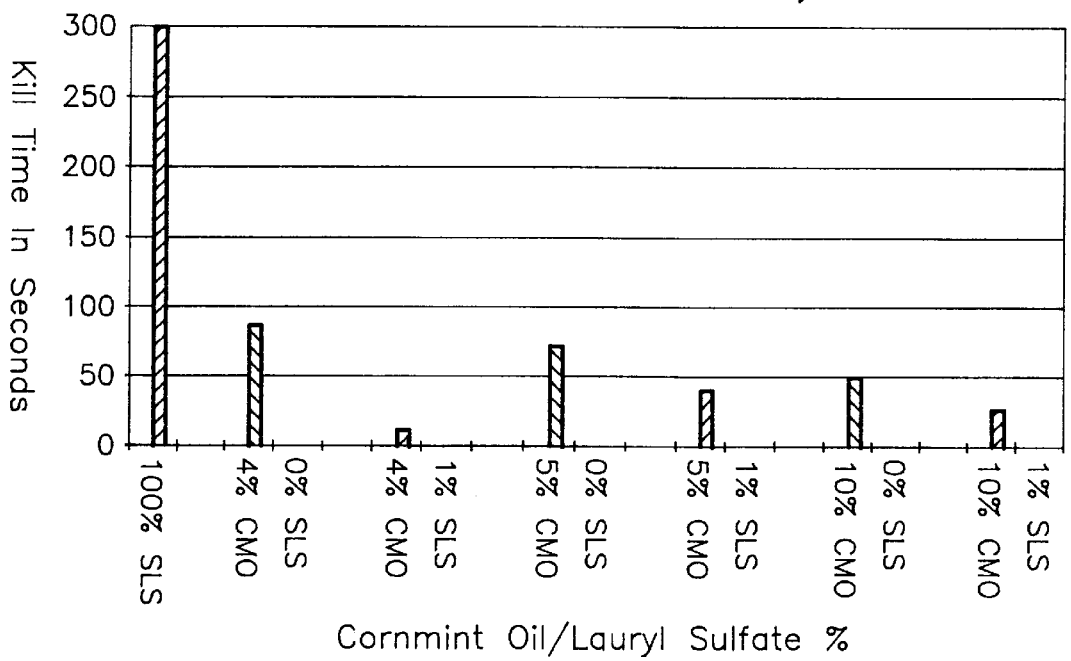
FIG. 3 is a bar graph illustrating the insecticidal effects of combining cornmint oil with sodium lauryl sulfate in killing black ants.

As seen from the data in Table 3 and illustrated in FIG. 3, similar unexpectedly reduced kill times are realized when the synergistic insecticidal composition of this invention is tested against black ants and compared with either ingredient alone. The 4% cornmint oil, 1% sodium lauryl sulfate composition of Test No. 17 is even more effective than compositions containing higher concentrations of the cornmint oil, a phenomenon believed to result from the density of the oil and the small body mass of the ants.

In summary, the foregoing test results establish that the individual components of one of the preferred insecticidal compositions of this invention, namely cornmint oil and sodium lauryl sulfate, are either ineffective, or relatively ineffective, in killing the targeted insect pests, whereas the combination of these materials unexpectedly killed substantially all insects contacted with the composition, and did so in a matter of seconds. For example, the addition of 1% sodium lauryl sulfate to 5% cornmint oil decreases the kill time of American cockroaches from "not effective" (over 300 seconds) to 42.2 seconds; the addition of 1% sodium lauryl sulfate to 5% cornmint oil decreases the kill time of German cockroaches from 39.8 seconds to 14.2 seconds; and the addition of 1% sodium lauryl sulfate to 4% cornmint oil decreases the kill time of black ants from 87 seconds to 12.9 seconds. Moreover, the kill time, as compared to a conventional aerosol insecticide incorporating poisonous active ingredients, was substantially the same or significantly reduced with the synergistic insecticidal composition of the instant invention.

The concentrations of the active ingredients in this cornmint oil/sodium lauryl sulfate composition can be widely varied while producing a highly effective, non-poisonous, fast-acting, broad spectrum insecticide according to this invention. Formulations can incorporate from about 0.1% to about 20% by volume of cornmint oil and from about 0.01% to about 30% sodium lauryl sulfate, the remainder comprising inert ingredients such as water, mineral oil and/or a propellant. Preferred compositions include from about 2% to about 10% cornmint oil with about 0.1% to about 2% sodium lauryl sulfate.

Compositions containing 4% cornmint oil and 0.1% sodium lauryl sulfate have been found to be highly effective in killing flying insects, such as flies, mosquitoes, gnats, moths, yellow jackets and bees, as well as crawling insects such as ants, roaches, both German and American cockroaches, water bugs, silverfish, crickets, spiders and centipedes.

A preferred composition for general use comprises about 4% cornmint oil and about 1% sodium lauryl sulfate, the remainder being inert ingredients such as water, mineral oil, if desired, and a propellant such as carbon dioxide.

By increasing the concentration of the cornmint oil to, for example, about 8%, a more effective kill ratio is found for resistant flying insects such as wasps, hornets, yellow jackets and other bees. A composition of this nature can kill such targeted insect pests in a matter of seconds. Entire nests of such flying insects can be killed by spraying the aerosol into the nest opening until the nest is saturated.

Although this insecticidal composition of the instant invention is useful in an open, outdoor environment, it is also safe and effective for use indoors, even in a relatively confined area. The composition will not stain carpets or floors, is non-poisonous, and has a fresh mint scent.

Cinnamon Oil

TABLE 4

The Effects of Cinnamon Oil and Lauryl Sulfate on German Cockroaches

| Test No. | Active Ingredients (Volume %) | Kill Time (Seconds) |
|---|---|---|
| 22. | 100% SLS | 300 |
| 23. | 1% Cinnamon Oil (CinO) 0% SLS | 300 |
| 24. | 1% CinO 1% SLS | 44.9 |
| 25. | 3% CinO 0% SLS | 300 |
| 26. | 3% CinO 1% SLS | 41.3 |
| 27. | 5% CinO 0% SLS | 300 |
| 28. | 5% CinO 1% SLS | 29 |

TABLE 5

The Effects of Cinnamon Oil and Lauryl Sulfate on American Cockroaches

| Test No. | Active Ingredients (Volume %) | Kill Time (Seconds) |
|---|---|---|
| 29. | 100% SLS | 300 |
| 30. | 1% CinO 0% SLS | 300 |
| 31. | 1% CinO 1% SLS | 300 |
| 32. | 3% CinO 0% SLS | 300 |
| 33. | 3% CinO 1% SLS | 300 |
| 34. | 5% CinO 0% SLS | 300 |
| 35. | 5% CinO 1% SLS | 300 |

TABLE 6

The Effects of Cinnamon Oil and Lauryl Sulfate on Black Ants

| Test No. | Active Ingredients (Volume %) | Kill Time (Seconds) |
|---|---|---|
| 36. | 100% SLS | 300 |
| 37. | 1% CinO 0% SLS | 108.4 |
| 38. | 1% CinO 1% SLS | 38.3 |
| 39. | 3% CinO 0% SLS | 111.7 |
| 40. | 3% CinO 1% SLS | 55.3 |
| 41. | 5% CinO 0% SLS | 300 |
| 42. | 5% CinO 1% SLS | 108 |

Figure 6:
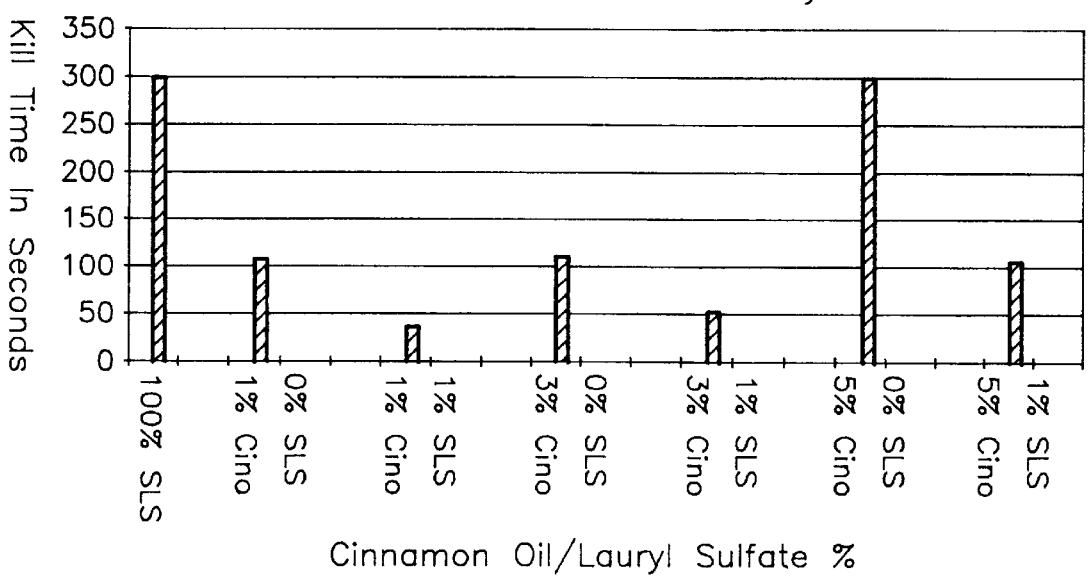
FIG. 6 is a bar graph illustrating the insecticidal effects of combining cinnamon oil with sodium lauryl sulfate in killing black ants.
Figure 4:
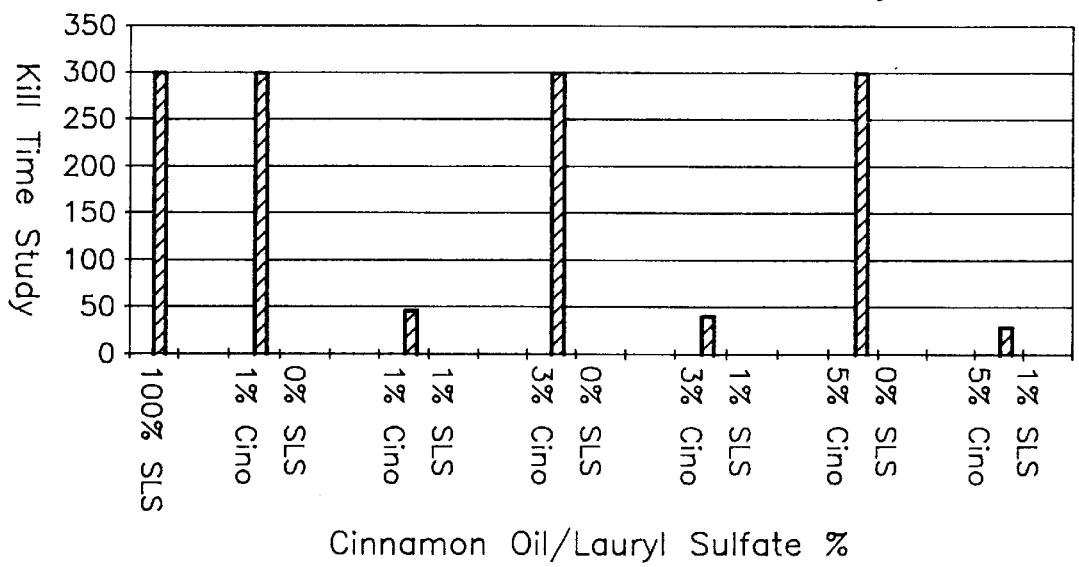
FIG. 4 is a bar graph illustrating the insecticidal effects of combining cinnamon oil with sodium lauryl sulfate in killing German cockroaches.
Figure 5:
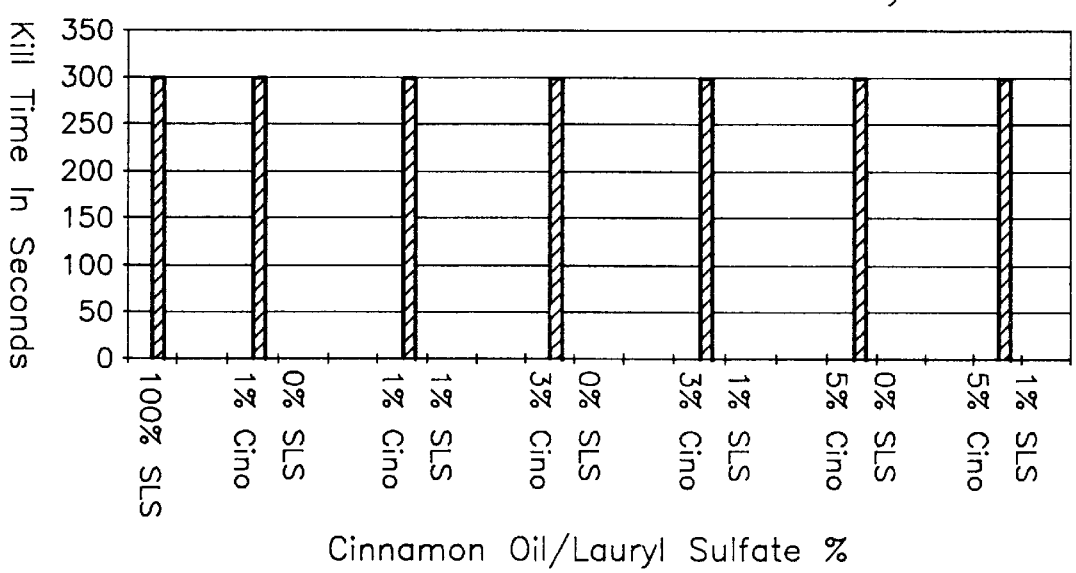
FIG. 5 is a bar graph illustrating the insecticidal effects of combining cinnamon oil with sodium lauryl sulfate in killing American cockroaches.
Figure 8:
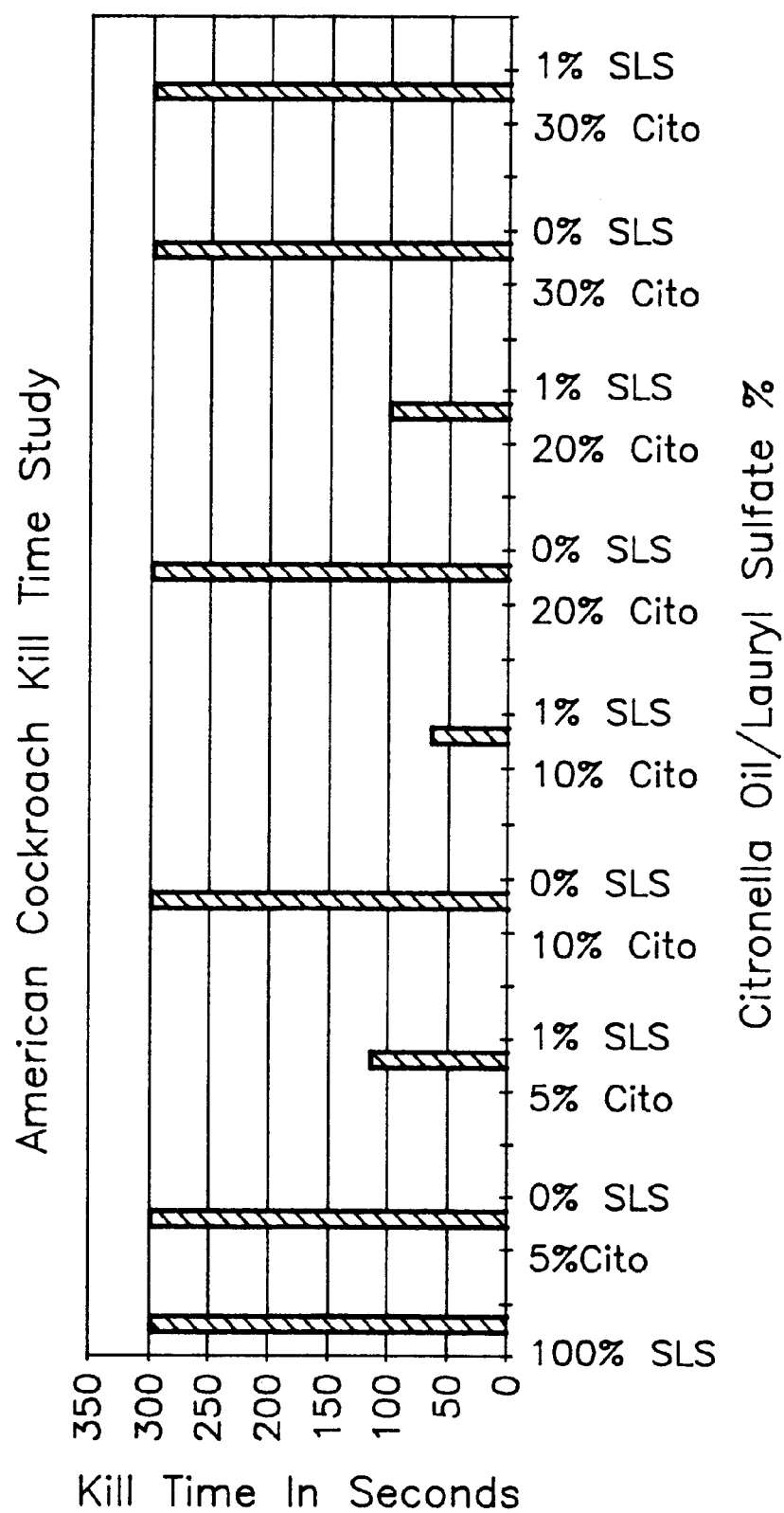
FIG. 8 is a bar graph illustrating the insecticidal effects of combining citronella oil with sodium lauryl sulfate in killing American cockroaches.

As seen from Tables 4–6 and illustrated in FIGS. 4–6, unlike cornmint oil, cinnamon oil shows selective synergistic results when combined with sodium lauryl sulfate. For example, when tested against German cockroaches, a definite synergy is seen between cinnamon oil and sodium lauryl sulfate alone with each oil concentration. Cinnamon oil alone (Test Nos. 23, 25 and 27), even at 5%, was ineffective, as was sodium lauryl sulfate (Test No. 22). Yet, with the addition of 1% sodium lauryl sulfate to the cinnamon oil, at each of the 1%, 3% and 5% concentration levels, the kill time was reduced significantly, to less than one minute in each test, and under one-half minute at the 5% level (Test No. 28).

In contrast, the combination of cinnamon oil and sodium lauryl sulfate showed no synergistic results when tested against American cockroaches, i.e., up to the 300 second standard time test allotted.

In the black ant test, a synergistic improvement in insecticidal activity is seen at all concentrations, but the kill time increases, rather than decreases, as might have been expected, with increased concentrations of cinnamon oil. As with the cornmint oil, this anomaly is believed to be the result of the density of the cinnamon oil and the small body mass of the ants. Thus, surprisingly, for an ant spray, even better results can be obtained with the use of less cinnamon oil when combined with the sodium lauryl sulfate synergist.

In general, it is believed that a composition comprising from about 0.01 to about 30% cinnamon oil with from about 0.01 to about 20% sodium lauryl sulfate, the remainder comprising inert ingredients, will be effective as a broad spectrum insecticide with synergistic activity. Preferred compositions include from about 1 to 20% cinnamon oil and about 0.1 to 5% sodium lauryl sulfate.

Citronella Oil

TABLE 7

The Effects of Citronella Oil and Lauryl Sulfate on German Cockroaches

| Test No. | Active Ingredients (Volume %) | Kill Time (Seconds) |
|---|---|---|
| 43. | 100% SLS | 300 |
| 44. | 5% Citronella Oil (CitO) 0% SLS | 60.3 |
| 45. | 5% CitO 1% SLS | 23.2 |
| 46. | 10% CitO 0% SLS | 57.1 |
| 47. | 10% CitO 1% SLS | 24.5 |
| 48. | 20% CitO 0% SLS | 29.9 |
| 49. | 20% CitO 1% SLS | 24.1 |
| 50. | 30% CitO 0% SLS | 31.5 |
| 51. | 30% CitO 1% SLS | 27.2 |

TABLE 8

The Effects of Citronella Oil and Lauryl Sulfate on American Cockroaches

| Test No. | Active Ingredients (Volume %) | Kill Time (Seconds) |
|---|---|---|
| 52. | 100% SLS | 300 |
| 53. | 5% CitO 0% SLS | 300 |
| 54. | 5% CitO 1% SLS | 113.9 |
| 55. | 10% CitO 0% SLS | 300 |
| 56. | 10% CitO 1% SLS | 63.8 |
| 57. | 20% CitO 0% SLS | 300 |

TABLE 8-continued

The Effects of Citronella Oil and Lauryl Sulfate on American Cockroaches

| Test No. | Active Ingredients (Volume %) | Kill Time (Seconds) |
|---|---|---|
| 58. | 20% CitO 1% SLS | 96.6 |
| 59. | 30% CitO 0% SLS | 300 |
| 60. | 30% CitO 1% SLS | 300 |

TABLE 9

The Effects of Citronella Oil and Lauryl Sulfate on Pavement Ants

| Test No. | Active Ingredients (Volume %) | Kill Time (Seconds) |
|---|---|---|
| 61. | 100% SLS | 300 |
| 62. | 5% Citronella Oil (CitO) 0% SLS | 42 |
| 63. | 5% CitO 1% SLS | 28.6 |
| 64. | 10% CitO 0% SLS | 69.9 |
| 65. | 10% CitO 1% SLS | 46.6 |
| 66. | 20% CitO 0% SLS | 65.2 |
| 67. | 20% CitO 1% SLS | 52.3 |
| 68. | 30% CitO 0% SLS | 71.9 |
| 69. | 30% CitO 1% SLS | 38.4 |

Citronella oil was tested at concentrations of 5, 10, 20 and 30% and demonstrated synergy with the sodium lauryl sulfate dilution at all oil concentrations for all insect species tested. However, the number progression is unique for each insect population. For both German cockroaches and pavement ants, the 5% citronella oil level is better than at all other concentrations.

With American cockroaches, Table No. 8 and FIG. No. 8, an increased kill rate is seen at the 5% concentration level, with even better results being seen at 10%, and the results then deteriorating at the 20 and 30% level.

Thus, the citronella oil test results illustrate the somewhat unexpected and unpredictable nature of the synergistic action when sodium lauryl sulfate is added at varying concentrations of these essential oils and the resultant composition is tested against different insect populations.

It is believed that a composition comprising from about 0.01 to about 30% citronella oil with from about 0.01 to about 20% sodium lauryl sulfate, the remainder comprising inert ingredients, will be commercially useful as a broad spectrum insecticide. Preferred compositions include from about 1 to 20% citronella oil and about 0.1 to 5% sodium lauryl sulfate.

Peppermint Oil

TABLE 10

The Effects of Peppermint Oil and Lauryl Sulfate on German Cockroaches

| Test No. | Active Ingredients (Volume %) | Kill Time (Seconds) |
|---|---|---|
| 70. | 100% SLS | 300 |
| 71. | 1% Peppermint Oil (PO) 0% SLS | 300 |
| 72. | 1% PO 1% SLS | 36.21 |
| 73. | 5% PO 0% SLS | 300 |
| 74. | 5% PO 1% SLS | 35.26 |
| 75. | 10% PO 0% SLS | 42.43 |
| 76. | 10% PO 1% SLS | 24.5 |

TABLE 11

The Effects of Peppermint Oil and Lauryl Sulfate on American Cockroaches

| Test No. | Active Ingredients (Volume %) | Kill Time (Seconds) |
|---|---|---|
| 77. | 100% SLS | 300 |
| 78. | 1% PO 0% SLS | 300 |
| 79. | 1% PO 1% SLS | 300 |
| 80. | 5% PO 0% SLS | 300 |
| 81. | 5% PO 1% SLS | 300 |
| 82. | 10% PO 0% SLS | 300 |
| 83. | 10% PO 1% SLS | 300 |

TABLE 12

The Effects of Peppermint Oil and Lauryl Sulfate on Pavement Ants

| Test No. | Active Ingredients (Volume %) | Kill Time (Seconds) |
|---|---|---|
| 84. | 100% SLS | 300 |
| 85. | 1% PO 0% SLS | 300 |
| 86. | 1% PO 1% SLS | 300 |
| 87. | 5% PO 0% SLS | 75.89 |
| 88. | 5% PO 1% SLS | 29.57 |
| 89. | 10% PO 0% SLS | 80.92 |
| 90. | 10% PO 1% SLS | 52.06 |

The combination of peppermint oil and sodium lauryl sulfate provided synergy at all tested concentrations (1, 5 and 10%. peppermint oil) when tested against German cockroaches and the kill times decreased as the concentration of oil increased. See Table 10 and FIG. 10, and compare Test Nos. 72, 74 and 76 with Test Nos. 71, 73 and 75, respectively.

In contrast, the addition of sodium lauryl sulfate to peppermint oil, at all tested concentrations, showed no insecticidal activity within the standard 300 second time allotted, against American cockroaches. See Table 11 and FIG. 11.

Figure 12:
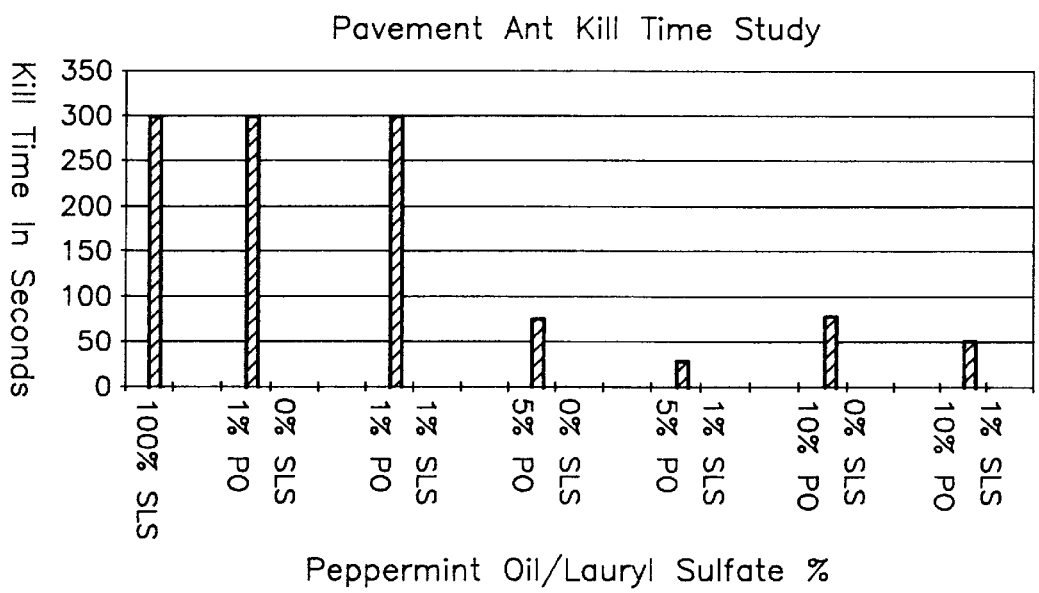
FIG. 12 is a bar graph illustrating the insecticidal effects of combining peppermint oil with sodium lauryl sulfate in killing pavement ants.

In Table 12 and FIG. 12, it will be seen that, at a 1% peppermint oil/1% sodium lauryl sulfate level, the composition was ineffective against pavement ants. Synergism was shown, however, at both the 5 and 10% level, with the 10% level showing an increased kill time consistent with the use of the other compositions tested herein in treating ants.

With peppermint oil from about 0.01 to about 30% combined with from about 0.01 to about 20% sodium lauryl sulfate is expected to evidence synergistic insecticidal activity. Preferred compositions comprise from about 1 to 20% peppermint oil with about 0.1 to 5% sodium lauryl sulfate.

Orange Sweet Oil

TABLE 13

The Effects of Orange Sweet Oil and Lauryl Sulfate on German Cockroaches

| Test No. | Active Ingredients (Volume %) | Kill Time (Seconds) |
|---|---|---|
| 91. | 100% SLS | 300 |
| 92. | 3% Orange Sweet Oil (OSO) 0% SLS | 47.8 |
| 93. | 3% OSO 1% SLS | 61 |
| 94. | 5% OSO 0% SLS | 31 |
| 95. | 5% OSO 1% SLS | 20.4 |
| 96. | 10% OSO 0% SLS | 23.7 |
| 97. | 10% OSO[4] 1% SLS | 23.3 |

[4]Due to insignificant improvement, the repetitions of the 10% orange sweet oil mixture on German cockroaches, were not performed.

TABLE 14

The Effects of Orange Sweet Oil and Lauryl Sulfate on American Cockroaches

| Test No. | Active Ingredients (Volume %) | Kill Time (Seconds) |
|---|---|---|
| 98. | 100% SLS | 300 |
| 99. | 3% OSO 0% SLS | 300 |
| 100. | 3% OSO 1% SLS | 300 |
| 101. | 5% OSO 0% SLS | 300 |
| 102. | 5% OSO 1% SLS | 300 |
| 103. | 10% OSO 0% SLS | 95.6 |
| 104. | 10% OSO 1% SLS | 68.6 |

TABLE 15

The Effects of Orange Sweet Oil and Lauryl Sulfate on Black Ants

| Test No. | Active Ingredients (Volume %) | Kill Time (Seconds) |
|---|---|---|
| 105. | 100% SLS | 300 |
| 106. | 3% OSO 0% SLS | 300 |
| 107. | 3% OSO 1% SLS | 300 |
| 108. | 5% OSO 0% SLS | 91.4 |
| 109. | 5% OSO 1% SLS | 16 |

Figure 13:
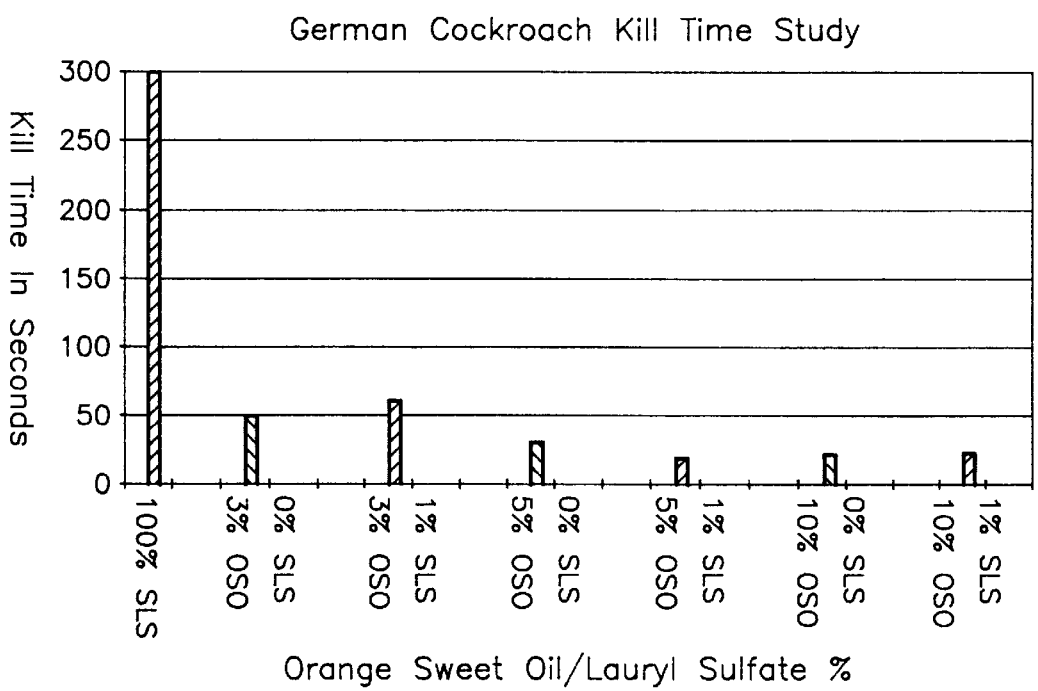
FIG. 13 is a bar graph illustrating the insecticidal effects of combining orange sweet oil with sodium lauryl sulfate in killing German cockroaches.
Figure 14:
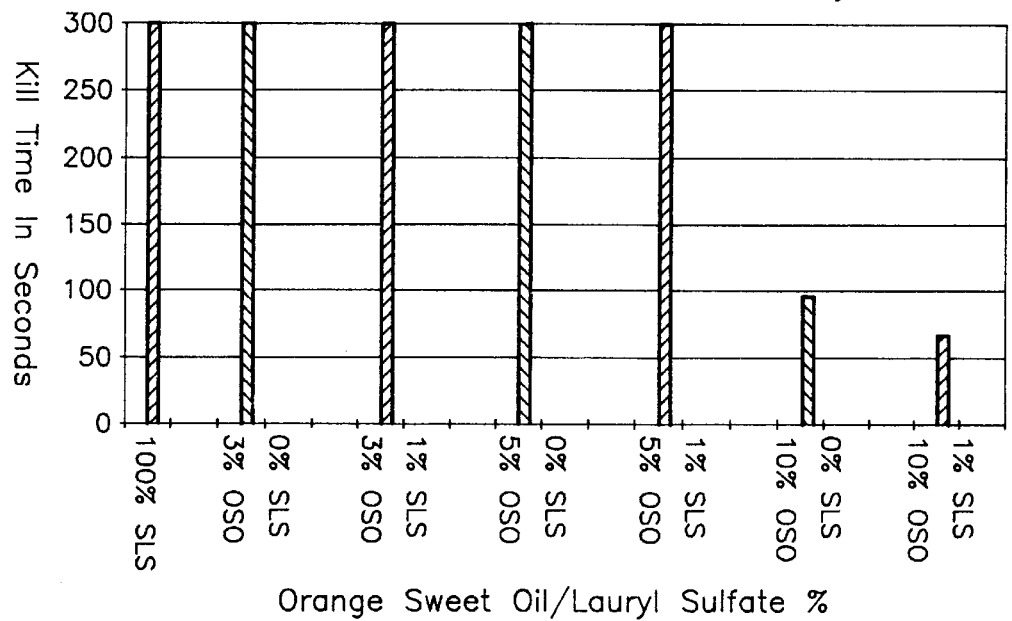
FIG. 14 is a bar graph illustrating the insecticidal effects of combining orange sweet oil with sodium lauryl sulfate in killing American cockroaches.

Orange sweet oil, a material not currently deregulated by the EPA, was tested at concentrations of 3, 5 and 10%, with 1% sodium lauryl sulfate against cockroaches[5]. As seen in Table 13 and FIG. 13, orange sweet oil alone, shows some insecticidal activity against German cockroaches, a 3% orange sweet oil composition being even more effective than a composition to which 1% sodium lauryl sulfate has been added. However, at 5% orange sweet oil, 1% sodium lauryl sulfate significantly reduces the kill time. Compare the 20.4 second kill time of Test No. 95, with the 31 second kill time of Test No. 94. Even more significant is the fact that at 5% orange sweet oil and 1% sodium lauryl sulfate, German cockroaches are killed more quickly than even a 10% orange sweet oil level without sodium lauryl sulfate. Compare Test No. 95 with Test No. 96.

[5]Due to the impressive results at the 5% level against ants, the 10% test was not pursued.

At a 10% level of orange sweet oil in combination with sodium lauryl sulfate, the kill time of American cockroaches was reduced by almost one-third. At lower levels, orange sweet oil does not kill American cockroaches, even in the presence of sodium lauryl sulfate.

Figure 15:
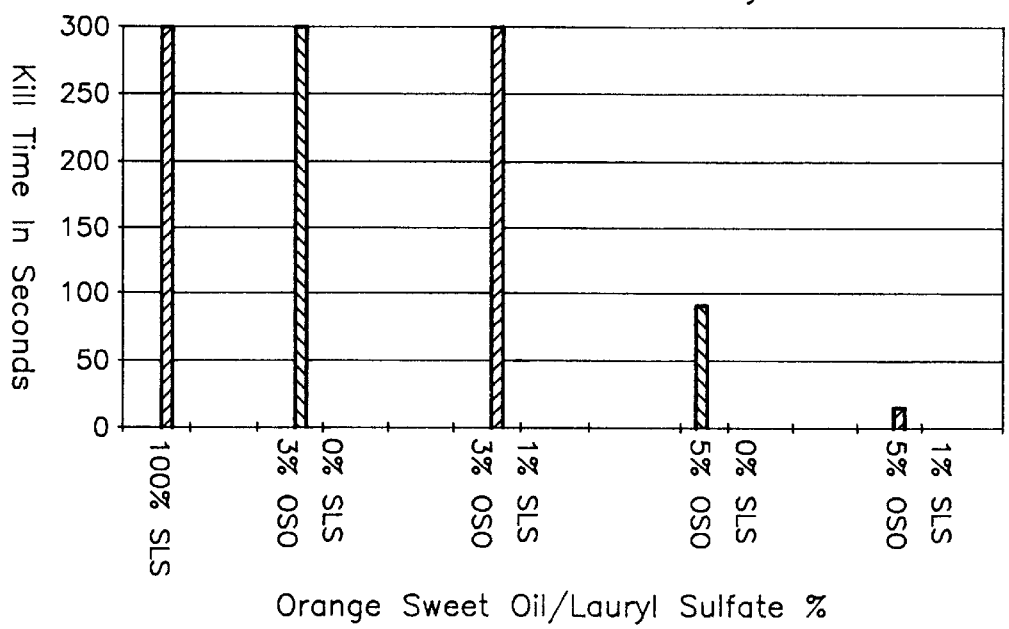
FIG. 15 is a bar graph illustrating the insecticidal effects of combining orange sweet oil with sodium lauryl sulfate in killing black ants.

Similarly, at a 3% level, orange sweet oil does not kill ants, but at a 5% orange sweet oil level, the kill time is dramatically reduced with the addition of 1% sodium lauryl sulfate. Compare Test Nos. 108 and 109 seen in Table 15 and FIG. 15.

A composition of from about 0.01 to about 80% orange sweet oil with from about 0.01 to about 20% sodium lauryl sulfate, the remainder comprising inert ingredients, is expected to be useful as a broad spectrum insecticide with synergistic activity. Preferred compositions of this insecticide may include from about 1 to 35% orange sweet oil and about 0.1 to 5% sodium lauryl sulfate.

Lemon Oil

TABLE 16

The Effects of Lemon Oil and Lauryl Sulfate on German Cockroaches

| Test No. | Active Ingredients (Volume %) | Kill Time (Seconds) |
|---|---|---|
| 110. | 100% SLS | 300 |
| 111. | 5% Lemon Oil (LeO) 0% SLS | 300 |
| 112. | 5% LeO 1% SLS | 90.24 |
| 113. | 10% LeO 0% SLS | 53.29 |

TABLE 16-continued

The Effects of Lemon Oil and Lauryl Sulfate on German Cockroaches

| Test No. | Active Ingredients (Volume %) | Kill Time (Seconds) |
| --- | --- | --- |
| 114. | 10% LeO 1% SLS | 47.21 |
| 115. | 20% LeO 0% SLS | 52.42 |
| 116. | 20% LeO 1% SLS | 29.27 |
| 117. | 30% LeO 0% SLS | 33.58 |
| 118. | 30% LeO 1% SLS | 32.84 |

TABLE 17

The Effects of Lemon Oil and Lauryl Sulfate on American Cockroaches

| Test No. | Active Ingredients (Volume %) | Kill Time (Seconds) |
| --- | --- | --- |
| 119. | 100% SLS | 300 |
| 120. | 5% LeO 0% SLS | 300 |
| 121. | 5% LeO 1% SLS | 300 |
| 122. | 10% LeO 0% SLS | 300 |
| 123 | 10% LeO 1% SLS | 300 |
| 124. | 20% LeO 0% SLS | 300 |
| 125. | 20% LeO 1% SLS | 300 |
| 126 | 30% LeO 0% SLS | 300 |
| 127. | 30% LeO 1% SLS | 77.84 |

TABLE 18

The Effects of Lemon Oil and Lauryl Sulfate on Pavement Ants

| Test No. | Active Ingredients (Volume %) | Kill Time (Seconds) |
| --- | --- | --- |
| 128. | 100% SLS | 300 |
| 129. | 5% LeO 0% SLS | 300 |
| 130. | 5% LeO 1% SLS | 51.39 |
| 131. | 10% LeO 0% SLS | 68.54 |
| 132. | 10% LeO 1% SLS | 52.82 |
| 133. | 20% LeO 0% SLS | 67.54 |
| 134. | 20% LeO 1% SLS | 54.18 |
| 135. | 30% LeO 0% SLS | 44.82 |
| 136. | 30% LeO 1% SLS | 43.87 |

Figure 16:
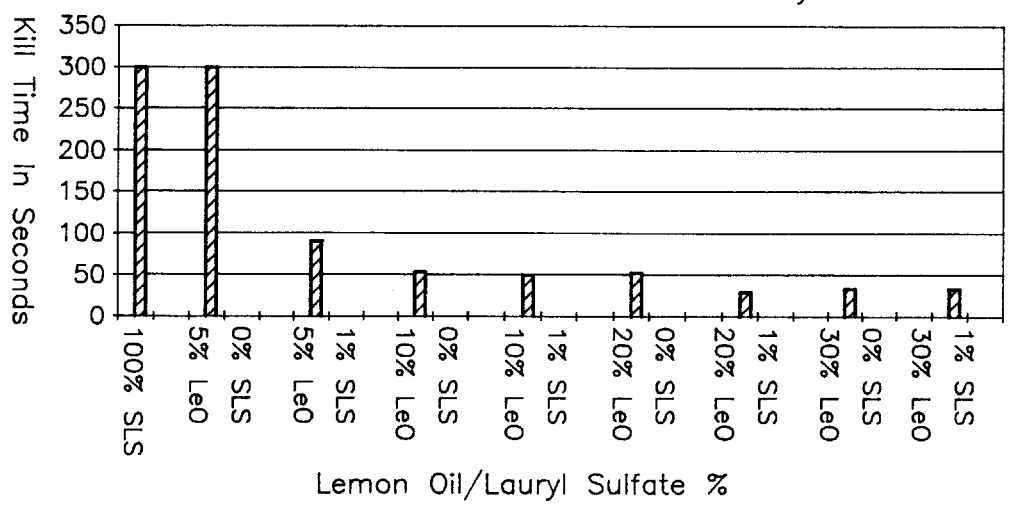
FIG. 16 is a bar graph illustrating the insecticidal effects of combining lemon oil with sodium lauryl sulfate in killing German cockroaches.
Figure 17:
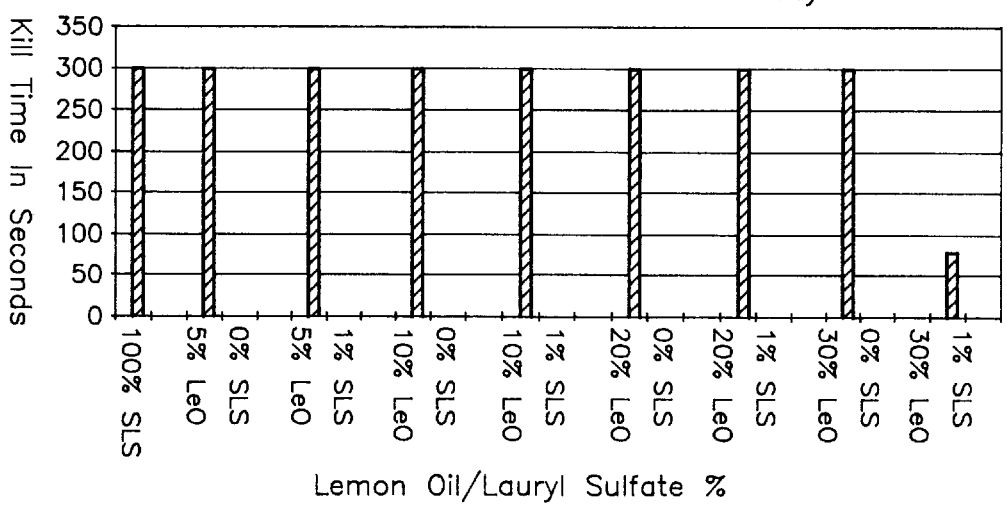
FIG. 17 is a bar graph illustrating the insecticidal effects of combining lemon oil with sodium lauryl sulfate in killing American cockroaches.
Figure 18:
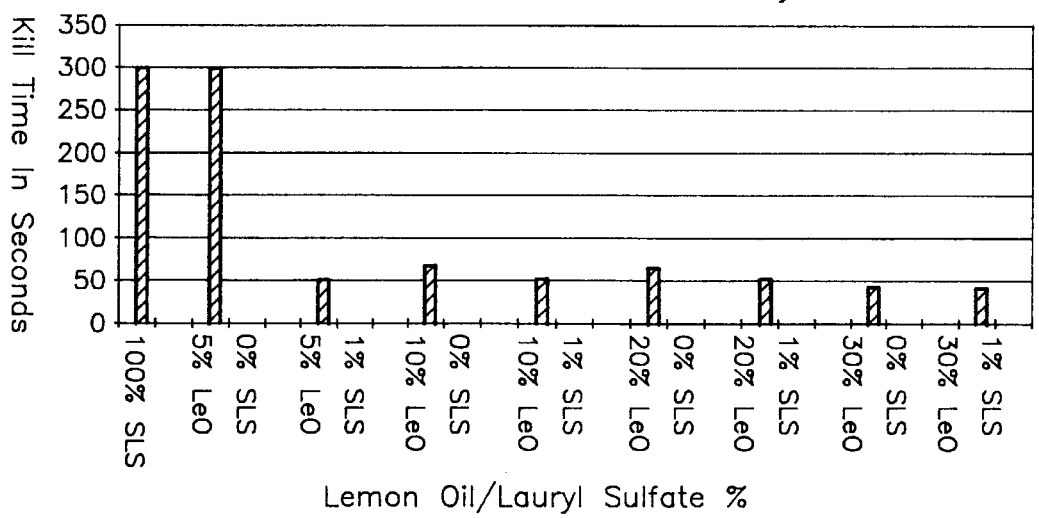
FIG. 18 is a bar graph illustrating the insecticidal effective of combining lemon oil with sodium lauryl sulfate in killing pavement ants.

Lemon oil was tested at concentrations of 5, 10, 20 and 30% and showed significant improved insecticidal activity with the addition of 1% sodium lauryl sulfate at the 5, 10 and 20% lemon oil concentrations for German cockroaches and pavement ants. Compare, for example, Test Nos. 112 and 114 with Test Nos. 113 and 115 in Table 16 and FIG. 16 for German cockroaches and Test Nos. 129 and 131 with Test Nos. 130 and 132 in Table 18 and FIG. 18 for pavement ants. At the 30% lemon oil level, the addition of sodium lauryl sulfate provided only a very limited improvement.

In contrast, with American cockroaches, it was only at the 30% concentration that a lemon oil and sodium lauryl sulfate composition was found to kill American cockroaches.

As with all of the essential citrus oils, from about 0.01 to about 80% of lemon oil combined with from about 0.01 to about 20% sodium lauryl sulfate can be expected to show synergistic activity, although preferred compositions are those containing from about 1 to 35% lemon oil and about 0.1 to 5% sodium lauryl sulfate.

Lime Oil

TABLE 19

The Effects of Lime Oil and Lauryl Sulfate on German Cockroaches

| Test No. | Active Ingredients (Volume %) | Kill Time (Seconds) |
| --- | --- | --- |
| 137. | 100% SLS | 300 |
| 138. | 5% Lime Oil (LiO) 0% SLS | 300 |
| 139. | 5% LiO 1% SLS | 49.34 |
| 140. | 10% LiO 0% SLS | 70.38 |
| 141. | 10% LiO 1% SLS | 48.78 |
| 142. | 20% LiO 0% SLS | 44.49 |
| 143. | 20% LiO 1% SLS | 29.43 |
| 144. | 30% LiO 0% SLS | 58.34 |
| 145. | 30% LiO 1% SLS | 28.61 |

TABLE 20

The Effects of Lime Oil and Lauryl Sulfate on American Cockroaches

| Test No. | Active Ingredients (Volume %) | Kill Time (Seconds) |
| --- | --- | --- |
| 146. | 100% SLS | 300 |
| 147. | 5% LiO 0% SLS | 300 |
| 148. | 5% LiO 1% SLS | 300 |
| 149. | 10% LiO 0% SLS | 300 |
| 150. | 10% LiO 1% SLS | 300 |
| 151. | 20% LiO 0% SLS | 300 |
| 152. | 20% LiO 1% SLS | 96.54 |
| 153. | 30% LiO 0% SLS | 300 |
| 154. | 30% LiO 1% SLS | 101.47 |

TABLE 21

The Effects of Lime Oil and Lauryl Sulfate on Pavement Ants

| Test No. | Active Ingredients (Volume %) | Kill Time (Seconds) |
|---|---|---|
| 155. | 100% SLS | 300 |
| 156. | 5% LiO 0% SLS | 101 |
| 157. | 5% LiO 1% SLS | 91.25 |
| 158. | 10% LiO 0% SLS | 101.75 |
| 159. | 10% LiO 1% SLS | 100.67 |
| 160. | 20% LiO 0% SLS | 300 |
| 161. | 20% LiO 1% SLS | 51.17 |
| 162. | 30% LiO 0% SLS | 101.77 |
| 163. | 30% LiO 1% SLS | 48.81 |

Figure 19:
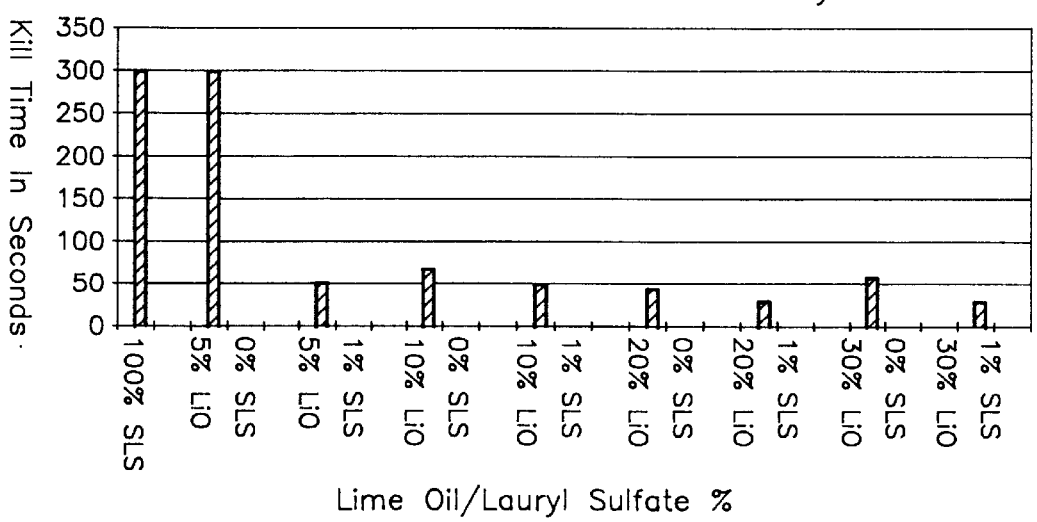
FIG. 19 is a bar graph illustrating the insecticidal effects of combining lime oil with sodium lauryl sulfate in killing German cockroaches.
Figure 20:
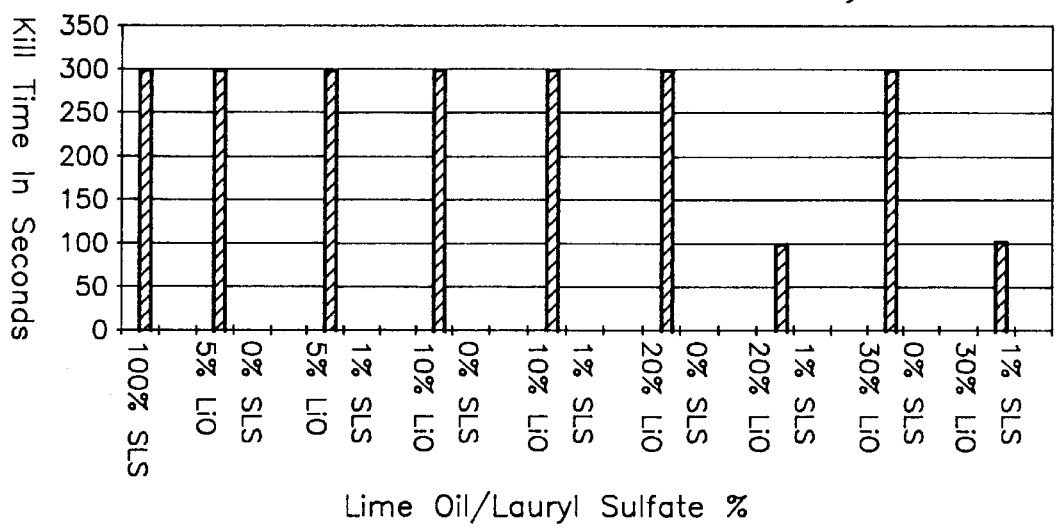
FIG. 20 is a bar graph illustrating the insecticidal effects of combining lime oil with sodium lauryl sulfate in killing American cockroaches.
Figure 21:
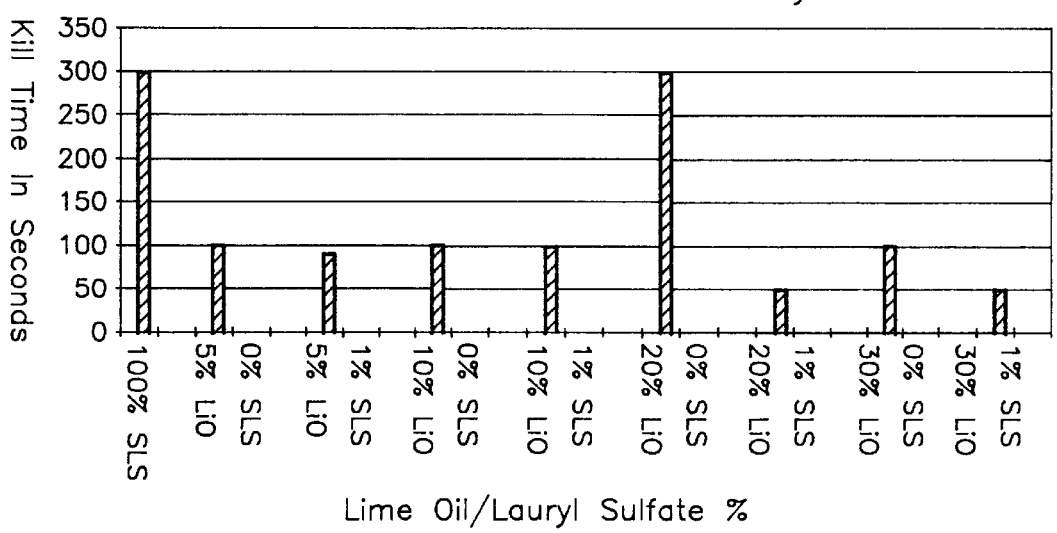
FIG. 21 is a bar graph illustrating the insecticidal effects of combining lime oil with sodium lauryl sulfate in killing pavement ants.

As shown in Tables 19–21 and FIGS. 19–21, synergy between lime oil and sodium lauryl sulfate is found for each of the tested insects at some levels. For German cockroaches at both the 5 and 10% lime oil levels, substantially the same kill time is seen. Compare Test Nos. 139 and 141. Similarly, at the 20 and 30% lime oil concentrations, similar kill times exist. Compare Test Nos. 143 and 145. In each instance, however, the kill times of compositions comprising lime oil and sodium lauryl sulfate are substantially less than the kill times for compositions comprising the same lime oil concentration, without sodium lauryl sulfate.

For American cockroaches, lime oil is seen to show significant synergism at the 20 and 30% level, when 1% sodium lauryl sulfate is added to the composition although the 20% level is even better than the 30% level. Compare Test Nos. 152 and 154 with each other and with Test Nos. 151 and 153, respectively.

For pavement ants, reduced kill times are found at all levels of lime oil with the addition of 1% sodium lauryl sulfate, although the improvement is relatively nominal at the 10% lime oil level. Yet, at the 20 and 30% lime oil level, lime oil alone is ineffective in killing pavement ants, whereas a composition comprising 1% sodium lauryl sulfate with the lime oil shows dramatic improvement. Compare Test Nos. 161 and 163 with Test Nos. 160 and 162, respectively.

The operable and optimum ranges of insecticidal compositions featuring lime oil are comparable to the other essential citrus oils.

Grapefruit Oil

TABLE 22

The Effects of Grapefruit Oil and Lauryl Sulfate on German Cockroaches

| Test No. | Active Ingredients (Volume %) | Kill Time (Seconds) |
|---|---|---|
| 164. | 100% SLS | 300 |
| 165. | 5% Grapefruit Oil (GO) 0% SLS | 97.91 |
| 166. | 5% GO 1% SLS | 50.25 |
| 167. | 10% GO 0% SLS | 88.92 |
| 168. | 10% GO 1% SLS | 29.7 |
| 169. | 20% GO 0% SLS | 53.61 |
| 170. | 20% GO 1% SLS | 34.07 |
| 171. | 30% GO 0% SLS | 64.14 |
| 172. | 30% GO 1% SLS | 29.99 |

TABLE 23

The Effects of Grapefruit Oil and Lauryl Sulfate on American Cockroaches

| Test No. | Active Ingredients (Volume %) | Kill Time (Seconds) |
|---|---|---|
| 173. | 100% SLS | 300 |
| 174. | 5% GO 0% SLS | 300 |
| 175. | 5% GO 1% SLS | 300 |
| 176. | 10% GO 0% SLS | 300 |
| 177. | 10% GO 1% SLS | 36.77 |
| 178. | 20% GO 0% SLS | 97.72 |
| 179. | 20% GO 1% SLS | 38.8 |
| 180. | 30% GO 0% SLS | 120 |
| 181. | 30% GO 1% SLS | 71.55 |

TABLE 24

The Effects of Grapefruit Oil and Lauryl Sulfate on Pavement Ants

| Test No. | Active Ingredients (Volume %) | Kill Time (Seconds) |
|---|---|---|
| 182. | 100% SLS | 300 |
| 183. | 5% GO 0% SLS | 36.49 |
| 184. | 5% GO 1% SLS | 35.46 |
| 185. | 10% GO 0% SLS | 50.45 |
| 186. | 10% GO 1% SLS | 27.8 |
| 187. | 20% GO 0% SLS | 34.38 |
| 188. | 20% GO 1% SLS | 32.86 |
| 189. | 30% GO 0% SLS | 38.17 |
| 190. | 30% GO 1% SLS | 35.61 |

Figure 22:
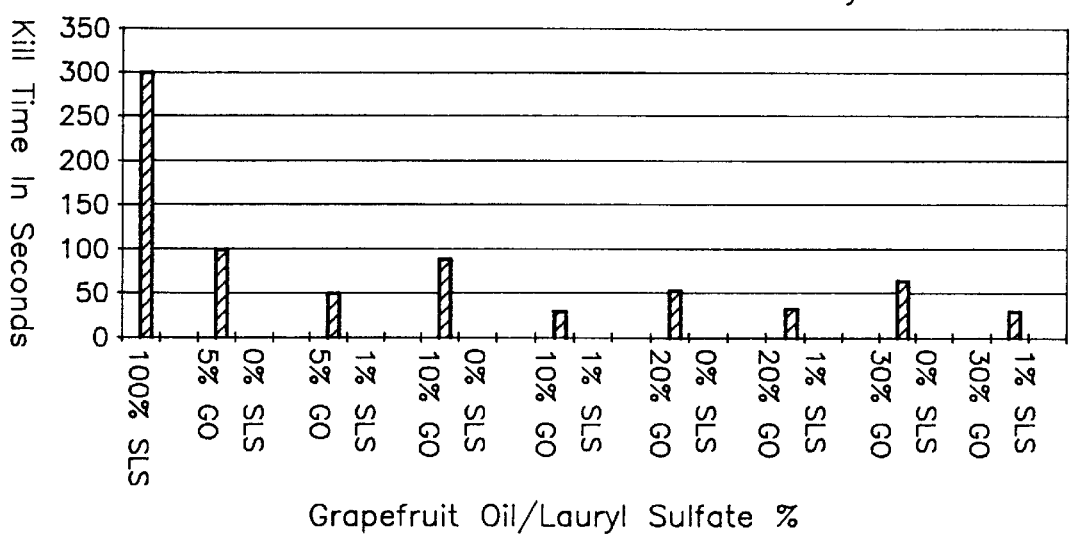
FIG. 22 is a bar graph illustrating the insecticidal effects of combining grapefruit oil with sodium lauryl sulfate in killing German cockroaches.
Figure 23:
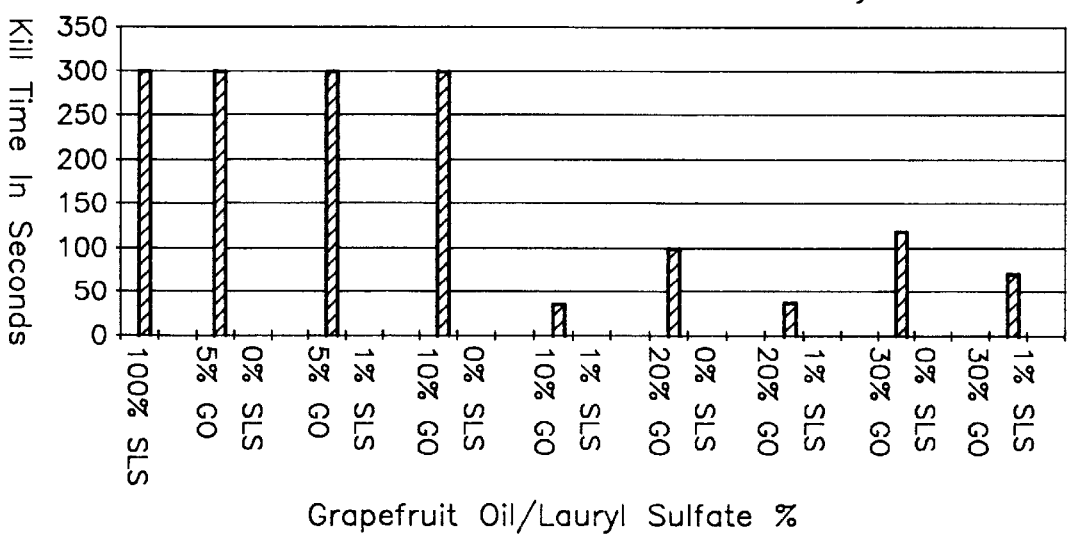
FIG. 23 is a bar graph illustrating the insecticidal effects of combining grapefruit oil with sodium lauryl sulfate in killing American cockroaches.
Figure 24:
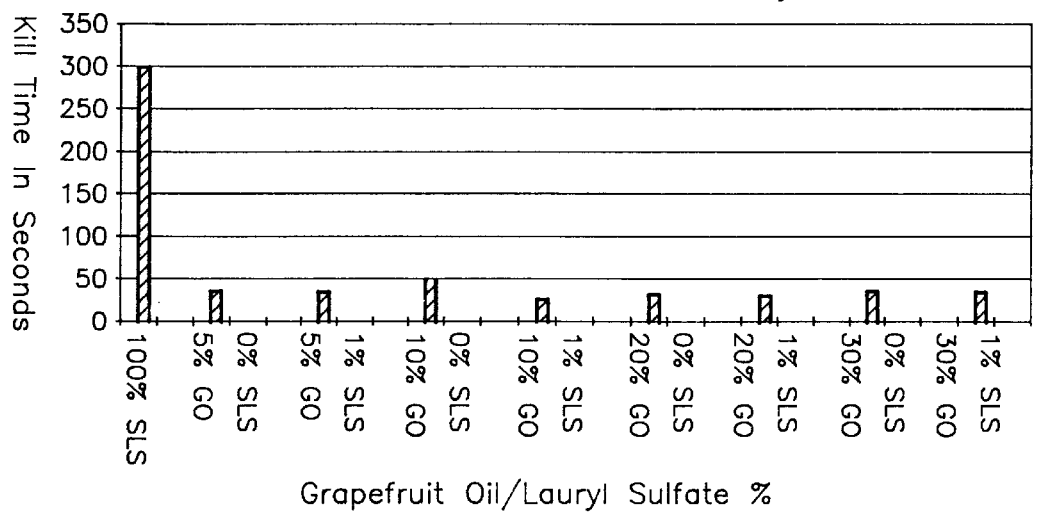
FIG. 24 is a bar graph illustrating the insecticidal effects of combining grapefruit oil with sodium lauryl sulfate in killing pavement ants.

Tables Nos. 22–24 and FIGS. 22–24 show that grapefruit oil is synergistically improved with the addition of 1% sodium lauryl sulfate at all concentrations on all test species, except for the American cockroach at an oil concentration of 5%. Particularly good results were found with 10% grapefruit oil for each of the insect species. See Test Nos. 168, 177 and 186.

Grapefruit oil is an essential citrus oil expected to function at similar levels to those described above.

Tangerine Oil

TABLE 25

The Effects of Tangerine Oil and Lauryl Sulfate on German Cockroaches

| Test No. | Active Ingredients (Volume %) | Kill Time (Seconds) |
| --- | --- | --- |
| 191. | 100% SLS | 300 |
| 192. | 5% Tangerine Oil (TO) 0% SLS | 32.07 |
| 193. | 5% TO 1% SLS | 50.34 |
| 194. | 10% TO 0% SLS | 26.3 |
| 195. | 10% TO 1% SLS | 46.58 |
| 196. | 20% TO 0% SLS | 42.24 |
| 197. | 20% TO 1% SLS | 64.72 |
| 198. | 30% TO 0% SLS | 39.2 |
| 199. | 30% TO 1% SLS | 63.36 |

TABLE 26

The Effects of Tangerine Oil and Lauryl Sulfate on American Cockroaches

| Test No. | Active Ingredients (Volume %) | Kill Time (Seconds) |
| --- | --- | --- |
| 200. | 100% SLS | 300 |
| 201. | 5% TO 0% SLS | 300 |
| 202. | 5% TO 1% SLS | 300 |
| 203. | 10% TO 0% SLS | 300 |
| 204. | 10% TO 1% SLS | 300 |
| 205. | 20% TO 0% SLS | 300 |
| 206. | 20% TO 1% SLS | 300 |
| 207. | 30% TO 0% SLS | 300 |
| 208. | 30% TO 1% SLS | 300 |

TABLE 27

The Effects of Tangerine Oil and Lauryl Sulfate on Pavement Ants

| Test No. | Active Ingredients (Volume %) | Kill Time (Seconds) |
| --- | --- | --- |
| 209. | 100% SLS | 300 |
| 210. | 5% TO 0% SLS | 300 |
| 211. | 5% TO 1% SLS | 63.06 |
| 212. | 10% TO 0% SLS | 300 |
| 213. | 10% TO 1% SLS | 87.35 |
| 214. | 20% TO 0% SLS | 300 |
| 215. | 20% TO 1% SLS | 48.33 |
| 216. | 30% TO 0% SLS | 111.55 |
| 217. | 30% TO 1% SLS | 51.61 |

Figure 25:
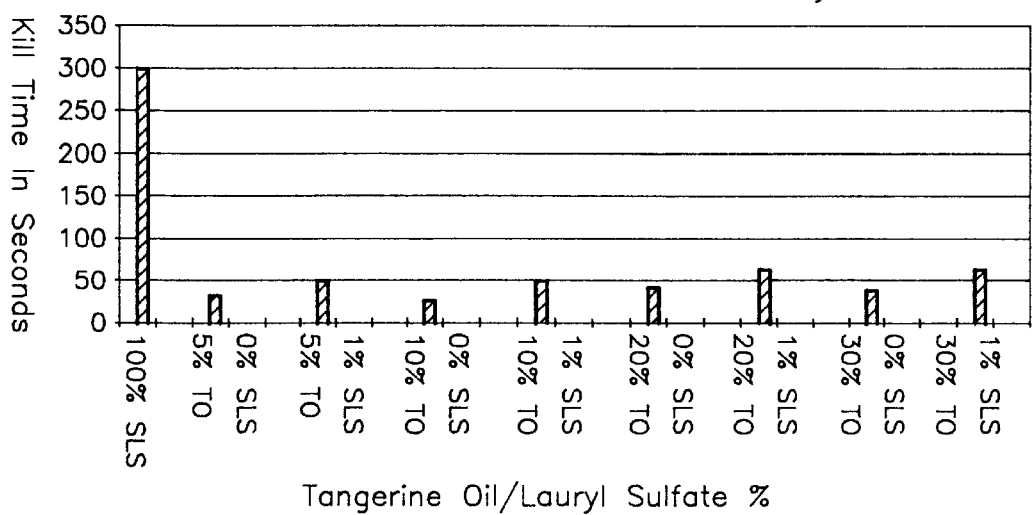
FIG. 25 is a bar graph illustrating the insecticidal effects of combining tangerine oil with sodium lauryl sulfate in killing German cockroaches.
Figure 26:
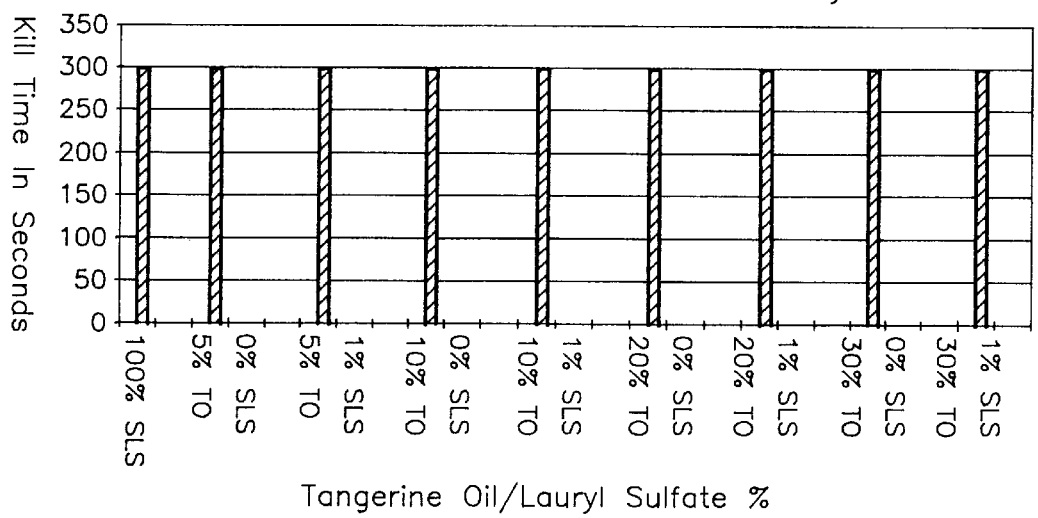
FIG. 26 is a bar graph illustrating the insecticidal effects of combining tangerine oil with sodium lauryl sulfate in killing American cockroaches.
Figure 27:
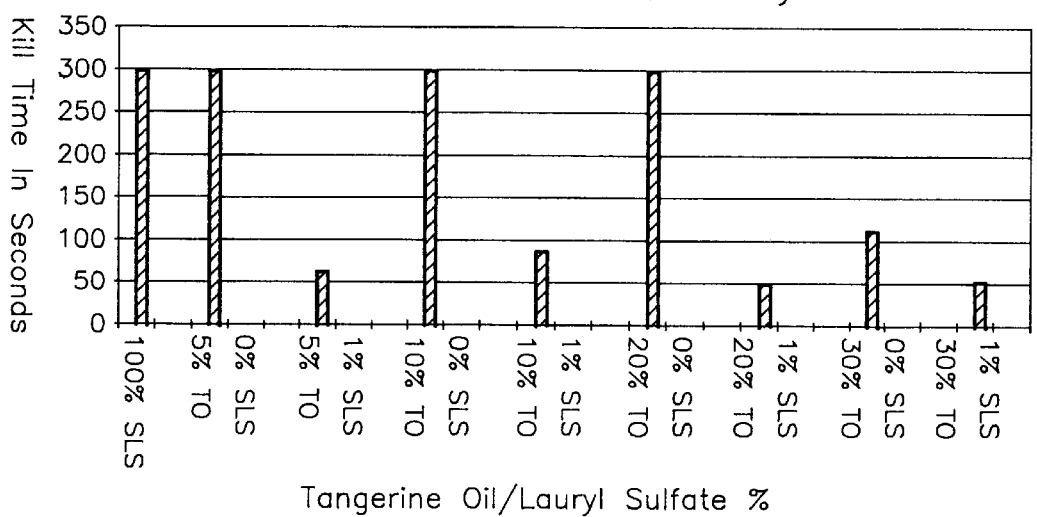
FIG. 27 is a bar graph illustrating the insecticidal effects of combining tangerine oil with sodium lauryl sulfate in killing pavement ants.

The test results with tangerine oil shown in Tables 25–27 and FIGS. 25–27, once again, illustrate the unpredictability of the effectiveness of these essential oils when combined with sodium lauryl sulfate. For example, for German cockroaches, as seen in Table 25 and FIG. 25, not only does the sodium lauryl sulfate show no synergistic improvement, but to the contrary, the tangerine oil was more effectious without its addition. Compare Test Nos. 192, 194, 196 and 198 to Test Nos. 193, 195, 197 and 199.

With American cockroaches, tangerine oil is ineffective, whether or not sodium lauryl sulfate is added to the composition.

Only with pavement ants is the addition of sodium lauryl sulfate significant in providing a synergistically improved kill time at every concentration of tangerine oil. Compare Test Nos. 211, 213, 215 and 217 with Test Nos. 210, 212, 214 and 216, respectively. Oddly, however, the kill times increase from the 5% to the 10% level, decrease at the 20% level, and increase again at the 30% level.

For an ant insecticide, tangerine oil is expected to be effective in compositions comprising from about 0.01 to about 80% tangerine oil with from about 0.01 to about 20% of sodium lauryl sulfate, preferred compositions including from about I to 35% tangerine oil with about 0.1 to 5% sodium lauryl sulfate.

The test data seen in Tables 1–27 and graphically illustrated in FIGS. 1–27 confirm that, for each of the essential oils tested, the addition of sodium lauryl sulfate provides synergistically improved results at least at some concentrations for some insect populations. While the specific nature of the improved synergistic activity is not predictable, now that it has been recognized that synergism exists between these essential oils and sodium lauryl sulfate, a determination of the particular concentrations of ingredients that are effective or best suited for specific insect species within the broad and preferred ranges set forth above can be readily determined by the simple protocol set forth above. Thus, one skilled in this art, recognizing the synergistic effect of sodium lauryl sulfate on these essential oils can select a particular composition, depending upon the insect or insects to be targeted, the specificity or breadth of the spectrum of insects to be killed by a single composition, the cost, and the availability of the active ingredients.

Although the foregoing test results have combined only a single essential oil with sodium lauryl sulfate at selected concentrations, it is evident that a combination of essential oils with sodium lauryl sulfate can be utilized and may show even better results, especially if a broad spectrum insecticide is desired.

Of the tested essential oils, cinnamon oil, citronella oil, cornmint oil and peppermint oil are currently deregulated.

As noted, various of the citrus oils have been proposed for deregulation, but are not currently accepted by the EPA as safe substances offering minimum risk in normal use. Deregulation is expected, however, in due course. Moreover, the synergistic activity identified above when these essential oils are combined with sodium lauryl sulfate may enable the use of a lower concentration of these ingredients in the production of an effective insecticide, minimizing any toxicity to humans and pets that may come in contact with such compositions.

In addition to the essential oils that have been tested and shown to be synergistically enhanced by the addition of sodium lauryl sulfate against at least some targeted insects, it is believed that certain other currently deregulated essential oils will also show increased insecticidal activity against at least some pest populations at some concentrations when combined with sodium lauryl sulfate. Among deregulated active ingredients currently available, in addition to those already tested as discussed hereinabove, cedar oil, clove oil, garlic oil, lemongrass oil, linseed oil, rosemary oil, soybean oil and thyme oil are all expected to exhibit such properties.

Cedar oil is expected to show synergistic results with similar levels of sodium lauryl sulfate as discussed above at levels of from about 0.01 to 30%, with a preferred composition comprising from about 0.5 to 10% cedar oil; for clove oil, the broad range would be from about 0.01 to 30%, with a preferred range of from about 1 to 20%; for garlic oil, the broad range would be from about 0.1 to 30%, with a preferred range of from about 1 to 20%; for lemongrass oil, the broad range would be from about 0.01 to 20%, with a preferred range of from about 0.5 to 5%; for linseed oil, the broad range would be from about 0.01 to 30%, with a preferred range of from about 1 to 20%; for rosemary oil, the broad range would be from about 0.01 to 30%, with a preferred range of from about 1 to 30%; for soybean oil the broad range would be from about 0.01 to 80%, with a preferred range of from about 1 to 30%; and for thyme oil, the broad range would be from about 0.01 to 30%, with a preferred range of from about 0.5 to 10%.

As mentioned above, in lieu of the tested sodium lauryl sulfate, lecithin, which is deregulated and considered to be an inert material by the EPA, is expected to function effectively as a synergist with the identified essential oils in operable and optimum proportions similar to those set forth for the sodium lauryl sulfate.

Having described the invention, many modifications thereto will become apparent to those skilled in the art to which it pertains without deviation from the spirit of the invention as defined by the scope of the appended claims.

We claim:

1. A method of controlling insect pests which comprises contacting the insect pests while the insects are flying or on a surface with an insecticidal composition consisting essentially of, as active ingredients, a combination of an citrus oil and a synergist, wherein the essential oil is selected from the group consisting of cinnamon oil, citronella oil, cedar oil, clove oil, garlic oil, lemongrass oil, linseed oil, rosemary oil, soybean oil, thyme oil, peppermint oil, and mixtures thereof, and the synergist is sodium lauryl sulfate, and wherein said citrus oil and synergist are present in an inert carrier in insecticidally synergistic proportions of at least 0.01 percent by volume of said citrus oil and 0.01 to 20 percent by volume of said synergist.

2. A method according to claim 1, wherein said citrus oil and synergist are in an aqueous solution.

3. A method according to claim 1, wherein said citrus oil is cinnamon oil, which is present at a concentration of from about 0.01 to 30 percent by volume.

4. A method according to claim 3, wherein the composition consists essentially of from about 1 to 20 percent cinnamon oil by volume and from about 0.1 to 5 percent by volume of said synergist.

5. A method according claim 1, wherein said citrus oil is citronella oil, which is present at a concentration of from about 0.01 to 30 percent by volume.

6. A method according to claim 5, wherein the composition consists essentially of from about 1 to 20 percent citronella oil by volume and from about 0.1 to 5 percent by volume of said synergist.

7. A method according claim 1, wherein said citrus oil is cedar oil, which is present at a concentration of from about 0.01 to 30 percent by volume.

8. A method according to claim 7, wherein the composition consists essentially of from about 0.5 to 10 percent cedar oil by volume and from about 0.1 to 5 percent by volume of said synergist.

9. A method according claim 1, wherein said citrus oil is clove oil, which is present at a concentration of from about 0.01 to 30 percent by volume.

10. A method according to claim 9, wherein the composition consists essentially of from about 1 to 20 percent clove oil by volume and from about 0.1 to 5 percent by volume of said synergist.

11. A method according claim 1, wherein said citrus oil is garlic oil, which is present at a concentration of from about 0.01 to 30 percent by volume.

12. A method according to claim 11, wherein the composition consists essentially of from about 1 to 20 percent garlic oil by volume and from about 0.1 to 5 percent by volume of said synergist.

13. A method according claim 1, wherein said citrus oil is lemongrass oil, which is present at a concentration of from about 0.01 to 20 percent by volume.

14. A method according to claim 13, wherein the composition consists essentially of from about 0.5 to 5 percent lemongrass oil by volume and from about 0.1 to 5 percent by volume of said synergist.

15. A method according claim 1, wherein said citrus oil is linseed oil, which is present at a concentration of from about 0.01 to 30 percent by volume.

16. A method according to claim 15, wherein the composition consists essentially of from about 1 to 20 percent linseed oil by volume and from about 0.1 to 5 percent by volume of said synergist.

17. A method according claim 1, wherein said citrus oil is rosemary oil, which is present at a concentration of from about 0.01 to 30 percent by volume.

18. A method according to claim 17, wherein the composition consists essentially of from about 1 to 20 percent rosemary oil by volume and from about 0.1 to 5 percent by volume of said synergist.

19. A method according claim 1, wherein said citrus oil is soybean oil, which is present at a concentration of from about 0.01 to 30 percent by volume.

20. A method according to claim 19, wherein the composition consists essentially of from about 1 to 30 percent soybean oil by volume and from about 0.5 to 5 percent by volume of said synergist.

21. A method according claim 1, wherein said citrus oil is thyme oil, which is present at a concentration of from about 0.01 to 30 percent by volume.

22. A method according to claim 21, wherein the composition consists essentially of from about 0.5 to 10 percent thyme oil by volume and from about 0.1 to 5 percent by volume of said synergist.

23. A method according claim 1, wherein said citrus oil is peppermint oil, which is present at a concentration of from about 0.01 to 30 percent by volume.

24. A method according to claim 23, wherein the composition consists essentially of from about 1 to 20 percent peppermint oil by volume and from about 0.1 to 5 percent by volume of said synergist.

25. A method of controlling insect pests which comprises contacting the insect pests while the insects are flying or on a surface with an insecticidal composition consisting essentially of, as active ingredients, a combination of an citrus oil and a synergist, wherein the citrus oil is selected from the group consisting of cinnamon oil, citronella oil, cedar oil, clove oil, garlic oil, lemongrass oil, linseed oil, rosemary oil, soybean oil, thyme oil, peppermint oil, cornmint oil, and mixtures thereof, and the synergist is lecithin, and wherein said citrus oil and synergist are present in an inert carrier in insecticidally synergistic proportions of at least 0.01 percent by volume of said citrus oil and at least 0.01 percent by volume of said synergist.

26. A method according to claim 25, wherein said citrus oil and synergist are in an aqueous solution.

27. A method according claim 25, wherein said citrus oil is cinnamon oil, which is present at a concentration of from about 0.01 to 30 percent by volume.

28. A method according to claim 27, wherein the cinnamon oil is present from about 1 to 20 percent by volume.

29. A method according claim 25, wherein said citrus oil is citronella oil, which is present at a concentration of from about 0.01 to 30 percent by volume.

30. A method according to claim 29, wherein the citronella oil is present from about 1 to 20 percent citronella oil by volume.

31. A method according claim 25, wherein said citrus oil is cedar oil, which is present at a concentration of from about 0.01 to 30 percent by volume.

32. A method according to claim 31, wherein the cedar oil is present from about 0.5 to 10 percent by volume.

33. A method according claim 25, wherein said citrus oil is clove oil, which is present at a concentration of from about 0.01 to 30 percent by volume.

34. A method according to claim 33, wherein the clove oil is present from about 1 to 20 percent by volume.

35. A method according claim 25, wherein said citrus oil is garlic oil, which is present at a concentration of from about 0.01 to 30 percent by volume.

36. A method according to claim 35, wherein the garlic oil is present from about 1 to 20 percent by volume.

37. A method according claim 25, wherein said citrus oil is lemongrass oil, which is present at a concentration of from about 0.01 to 20 percent by volume.

38. A method according to claim 37, wherein the lemongrass oil is present from about 0.5 to 5 percent by volume.

39. A method according claim 25, wherein said citrus oil is linseed oil, which is present at a concentration of from about 0.01 to 30 percent by volume.

40. A method according to claim 39, wherein the linseed oil is present from about 1 to 20 percent by volume.

41. A method according claim 25, wherein said citrus oil is rosemary oil, which is present at a concentration of from about 0.01 to 30 percent by volume.

42. A method according to claim 41, wherein the rosemary oil is present from about 1 to 20 percent by volume.

43. A method according claim 25, wherein said citrus oil is soybean oil, which is present at a concentration of from about 0.01 to 30 percent by volume.

44. A method according to claim 43, wherein the soybean oil is present from about 1 to 30 percent by volume.

45. A method according claim 25, wherein said citrus oil is thyme oil, which is present at a concentration of from about 0.01 to 30 percent by volume.

46. A method according to claim 45, wherein the thyme oil is present from about 0.5 to 10 percent by volume.

47. A method according claim 25, wherein said citrus oil is peppermint oil, which is present at a concentration of from about 0.01 to 30 percent by volume.

48. A method according to claim 47, wherein the peppermint oil is present from about 1 to 20 percent by volume.

49. A method according claim 25, wherein said citrus oil is cornmint oil, which is present at a concentration of from about 0.1 to 20 percent by volume.

50. A method according to claim 49, wherein the cornmint oil is present from about 2 to 10 percent by volume.

51. A method of controlling insect pests which comprises contacting the insect pests while the insects are flying or on a surface with an insecticidal composition consisting essentially of, as the active ingredients, a combination of a citrus oil and a synergist selected from the group consisting of sodium lauryl sulfate and lecithin, wherein said citrus oil and said synergist are present in an inert carrier in insecticidally synergistic proportions of from about 1–35 percent by volume of said citrus oil and from about 0.1–5 percent by volume of said synergist.

52. A method according to claim 51, wherein said citrus oil and said synergist are in an aqueous solution.

53. A method according to claim 51 wherein said synergist is sodium lauryl sulfate.

54. A method according to claim 51 wherein said synergist is lecithin.

55. The method of claim 51 wherein said citrus oil is grapefruit oil.

56. The method of claim 51 wherein said citrus oil is lemon oil.

57. The method of claim 51 wherein said citrus oil is lime oil.

58. The method of claim 51 wherein said citrus oil is orange sweet oil.

59. The method of claim 51 wherein said citrus oil is tangerine oil.

60. An insecticidal composition consisting essentially of, as the active ingredients, a combination, in insecticidally synergistic proportions, of an essential oil and a synergist, wherein said essential oil is cornmint oil and said synergist is lecithin and wherein said composition contains from about 0.1 to 20 percent by volume cornmint oil and from about 0.01 to 30% by volume lecithin.

61. The composition of claim 60 wherein the composition consists essentially of from about 2 to 10 percent by volume corn mint oil and from about 0.1 to 2 percent by volume lecithin.

62. A method of controlling insect pests which comprises contacting the insect pests with an insecticidally effective amount of a composition according to claim 60.

* * * * *

UNITED STATES PATENT AND TRADEMARK OFFICE
CERTIFICATE OF CORRECTION

PATENT NO. : 6,548,085 B1  Page 1 of 1
DATED : April 15, 2003
INVENTOR(S) : Karen A. Zobitne et al.

It is certified that error appears in the above-identified patent and that said Letters Patent is hereby corrected as shown below:

Column 23,
Lines 4, 5, 10 and 12, change "citrus" to -- essential --.
Lines 13, 15, 20, 26, 31, 35, 40, 44, 49 and 54, change "citrus" to -- essential --.

Column 24,
Lines 3, 8 and 13, change "citrus" to -- essential --.

Signed and Sealed this

Seventh Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,548,085 B1
DATED : April 15, 2003
INVENTOR(S) : Karen A. Zobitne et al.

It is certified that error appears in the above-identified patent and that said Letters Patent is hereby corrected as shown below:

Column 21,
Lines 52, 58, 60, 62, 64 and 67, change "citrus" to -- essential --.

Column 22,
Lines 9, 15, 22, 28, 35, 42, 48, 55 and 62, change "citrus" to -- essential --.

Column 23,
Lines 4, 5, 10 and 12, change "citrus" to -- essential --.
Lines 13, 15, 20, 26, 31, 40, 44, 49 and 54, change "citrus" to -- essential --.

Column 24,
Lines 3, 8 and 13, change "citrus" to -- essential --.

This certificate supersedes Certificate of Correction issued October 7, 2003.

Signed and Sealed this

First Day of February, 2005

JON W. DUDAS
*Director of the United States Patent and Trademark Office*